(12) United States Patent
Hodgdon et al.

(10) Patent No.: US 10,975,338 B2
(45) Date of Patent: *Apr. 13, 2021

(54) ACTIVE AGENT-CONTAINING THREE-DIMENSIONAL ARTICLES

(71) Applicant: The Procter & Gamble Company, Cincinnati, OH (US)

(72) Inventors: Travis Kyle Hodgdon, Cincinnati, OH (US); Mark William Hamersky, Hamilton, OH (US); Douglas Michael Graham, Cincinnati, OH (US); Paul Thomas Weisman, Cincinnati, OH (US); Michael Sean Farrell, Terrace Park, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 96 days.

This patent is subject to a terminal disclaimer.

(21) Appl. No.: 15/975,818

(22) Filed: May 10, 2018

(65) Prior Publication Data

US 2018/0334642 A1    Nov. 22, 2018

Related U.S. Application Data

(60) Provisional application No. 62/506,944, filed on May 16, 2017.

(51) Int. Cl.

| C11D 17/04 | (2006.01) |
| C11D 11/00 | (2006.01) |
| C11D 3/50  | (2006.01) |
| C11D 3/20  | (2006.01) |
| C11D 3/30  | (2006.01) |

(Continued)

(52) U.S. Cl.
CPC .......... *C11D 17/047* (2013.01); *A61K 8/0208* (2013.01); *A61K 8/342* (2013.01); *A61K 8/416* (2013.01); *A61Q 5/12* (2013.01); *B33Y 80/00* (2014.12); *C11D 3/2079* (2013.01); *C11D 3/30* (2013.01); *C11D 3/50* (2013.01); *C11D 3/505* (2013.01); *C11D 11/0017* (2013.01); *C11D 1/62* (2013.01)

(58) Field of Classification Search
CPC ............ C11D 17/04; C11D 11/00; C11D 3/30
See application file for complete search history.

(56) References Cited

U.S. PATENT DOCUMENTS

| 4,973,422 A * | 11/1990 | Schmidt ................. | C11D 3/505 |
| | | | 427/214 |
| 5,077,119 A * | 12/1991 | Wraige ................. | C11D 17/047 |
| | | | 427/242 |

(Continued)

OTHER PUBLICATIONS

All Office Actions U.S. Appl. No. 15/975,818.

(Continued)

*Primary Examiner* — Mark Eashoo
*Assistant Examiner* — M. Reza Asdjodi
(74) *Attorney, Agent, or Firm* — C. Brant Cook

(57) ABSTRACT

Active agent-containing 3D articles, for example dryer-added 3D articles and/or washing machine-added 3D articles and/or hair care 3D articles, and more particularly to consumable, single use, water-insoluble 3D articles containing one or more active agents and optionally, one or more auxiliary ingredients, methods for making same, and methods for using same are provided.

19 Claims, 7 Drawing Sheets

(51) Int. Cl.
*A61K 8/41* (2006.01)
*B33Y 80/00* (2015.01)
*A61K 8/02* (2006.01)
*A61K 8/34* (2006.01)
*A61Q 5/12* (2006.01)
*C11D 1/62* (2006.01)

(56) References Cited

U.S. PATENT DOCUMENTS

| | | | |
|---|---|---|---|
| 7,492,855 B2 * | 2/2009 | Hopkins | A61B 6/482 |
| | | | 378/10 |
| 7,820,614 B2 | 10/2010 | Tee, Jr. et al. | |
| 8,338,359 B2 | 12/2012 | Kenneally et al. | |
| 9,273,274 B2 | 3/2016 | Aouad et al. | |
| 2003/0114936 A1 * | 6/2003 | Sherwood | A61F 2/28 |
| | | | 623/23.58 |
| 2003/0195130 A1 | 10/2003 | Lentsch et al. | |
| 2004/0167056 A1 | 8/2004 | Lentsch et al. | |
| 2008/0004204 A1 | 1/2008 | Tindel-Koukal et al. | |
| 2008/0132437 A1 * | 6/2008 | Zhang | C11D 1/667 |
| | | | 510/102 |
| 2008/0146486 A1 * | 6/2008 | Boardman | C11D 3/001 |
| | | | 510/519 |
| 2009/0144913 A1 * | 6/2009 | Yu | C11D 3/001 |
| | | | 8/137 |
| 2010/0021528 A1 * | 1/2010 | Sackinger | A61L 15/18 |
| | | | 424/447 |
| 2011/0023240 A1 * | 2/2011 | Fossum | C11D 1/62 |
| | | | 8/137 |
| 2011/0269663 A1 * | 11/2011 | Clowes | C11D 1/62 |
| | | | 510/515 |
| 2012/0021026 A1 * | 1/2012 | Glenn, Jr. | A61K 9/70 |
| | | | 424/401 |
| 2012/0058166 A1 * | 3/2012 | Glenn, Jr. | D01F 1/10 |
| | | | 424/401 |
| 2012/0207805 A1 * | 8/2012 | Colman | A01N 33/12 |
| | | | 424/404 |
| 2015/0004865 A1 * | 1/2015 | Soyama | B01D 69/10 |
| | | | 442/392 |
| 2015/0126430 A1 * | 5/2015 | Ramirez | C11D 1/645 |
| | | | 510/513 |
| 2016/0250109 A1 * | 9/2016 | Dreher | A61K 8/0216 |
| | | | 424/401 |
| 2017/0342348 A1 | 11/2017 | Zhang et al. | |
| 2017/0349859 A1 | 12/2017 | Zhang et al. | |
| 2018/0334642 A1 * | 11/2018 | Hodgdon | C11D 17/047 |
| 2018/0334643 A1 * | 11/2018 | Hamersky | C11D 17/047 |
| 2018/0334644 A1 * | 11/2018 | Hamersky | C11D 17/047 |

OTHER PUBLICATIONS

All Office Actions U.S. Appl. No. 15/975,822.
All Office Actions U.S. Appl. No. 15/975,828.
U.S. Appl. No. 15/975,822, filed May 10, 2018, Hamersky, et al.
U.S. Appl. No. 15/975,828, filed May 10, 2018, Hamersky, et al.

* cited by examiner

ACTIVE AGENT-CONTAINING THREE-DIMENSIONAL ARTICLES

FIELD OF THE INVENTION

The present invention relates to active agent-containing three-dimensional (3D) articles, for example dryer-added 3D articles and/or washing machine-added 3D articles and/or hair care 3D articles, and more particularly to consumable, single use, water-insoluble 3D articles, for example dryer-added extruded 3D article and/or washing machine-added extruded 3D article and/or printed and/or extruded 3D hair care article, containing one or more active agents and optionally, one or more auxiliary ingredients, for example one or more structurants and/or one or more fillers, methods for making same, and methods for using same.

BACKGROUND OF THE INVENTION

Dryer-added articles in the past have consisted of a carrier sheet, such as a thermoplastic nonwoven sheet, for example a polyester nonwoven sheet that is coated and/or impregnated with a fabric conditioning active agent and/or a holder that affixes to a dryer's drum and contains a refillable solid fabric conditioning active agent, often referred to as a dryer bar. During use, the fabric conditioning active agent is at least partially transferred to (deposited on) fabrics being treated in a dryer. In the case of the carrier sheet containing the fabric conditioning active agent, remnants of the carrier sheet and/or other remains after use must be disposed of. In the case of the dryer bar, which is a multi-use article, the holder remains affixed to the dryer drum and oftentimes at least a portion of the fabric conditioning active agent remains attached to the holder, since it is a multi-use article.

One problem with existing dryer-added articles is that at least a portion of the existing dryer-added articles and/or holder remains in the dryer after use. In other words, at least a portion of the existing dryer-added articles and/or holder are not consumable after a single use in the dryer. The existing dryer-added articles with their excess, not consumed, material creates waste which must be disposed of.

Accordingly, there is a need for an active agent-containing 3D article, for example an active agent-containing dryer-added 3D article that overcomes the negatives described above by being a consumable, single use active agent-containing 3D article, for example a consumable, single use active agent-containing dryer-added 3D article, a method for making same, and a method for treating surfaces, such as fabrics with such an active agent-containing 3D article.

SUMMARY OF THE INVENTION

The present invention fulfills the needs described above by providing a consumable, single use active agent-containing 3D article, for example a consumable, single use active agent-containing dryer-added 3D article, a method for making same, and a method for using same.

One solution to the problem identified above is to provide a consumable, single use active agent-containing 3D article, for example a consumable, single use active agent-containing dryer-added 3D article that is consumed during use for treating fabrics in an automatic clothes dryer and/or in a washing machine wherein the water-insoluble 3D article may form a lamellar structure as measured by the Lamellar Structure Test Method described herein and/or a consumable, single use active agent-containing 3D article for treating hair.

In one example of the present invention, a consumable, single use 3D article, for example a consumable, single use, water-insoluble 3D article comprising:
  a. one or more active agents; and
  b. optionally, one or more auxiliary ingredients, for example one or more structurants, which function to increase the flow rheology and/or extensional rheology of the 3D article-forming composition used to make the 3D article, and/or one or more fillers, which function to increase only the flow rheology of the 3D article-forming composition;

wherein the 3D article exhibits a Bounding Box Density of less than about 0.98 and/or less than about 0.95 and/or less than about 0.80 and/or less than about 0.70 g/cm$^3$ as measured according to the μCT Test Method; and wherein the 3D article exhibits a 3D Article Free Melt Flow of greater than about 20% as measured according to the 3D Article Free Melt Flow Test Method, is provided.

In another example of the present invention, a consumable, single use 3D article, for example a consumable, single use, water-insoluble 3D article comprising:
  a. one or more active agents; and
  b. optionally, one or more auxiliary ingredients, for example one or more structurants, which function to increase the flow rheology and/or extensional rheology of the 3D article-forming composition used to make the 3D article, and/or one or more fillers, which function to increase only the flow rheology of the 3D article-forming composition;

wherein the 3D article exhibits a Surface Area to Volume Ratio of greater than about 0.10 and/or greater than about 0.20 and/or greater than about 0.30 and/or greater than about 0.40 and/or greater than about 0.50 and/or greater than about 0.60 and/or greater than about 0.70 and/or greater than about 0.80 and/or greater than about 0.90 and/or greater than about 1.00 mm$^{-1}$ as measured according to the μCT Test Method; and wherein the 3D article exhibits a 3D Article Free Melt Flow of greater than about 20% as measured according to the 3D Article Free Melt Flow Test Method, is provided.

In another example of the present invention, a method for making a consumable, single use 3D article, for example a consumable, single use, water-insoluble 3D article, the method comprising the steps of:
  a. providing a 3D article-forming composition comprising one or more active agents and optionally, one or more auxiliary ingredients, for example one or more structurants and/or one or more fillers; and
  b. producing a consumable, single use 3D article, for example a consumable, single use, water-insoluble 3D article from the 3D article-forming composition;

wherein the consumable, single use 3D article exhibits a Bounding Box Density of less than about 0.98 and/or less than about 0.95 and/or less than about 0.80 and/or less than about 0.70 g/cm$^3$ as measured according to the μCT Test Method; and wherein the consumable, single use 3D article exhibits a 3D Article Free Melt Flow of greater than about 20% as measured according to the 3D Article Free Melt Flow Test Method, is provided.

In still another example of the present invention, a method for making a consumable, single use 3D article, for example a consumable, single use, water-insoluble 3D article, the method comprising the steps of:
  a. providing a 3D article-forming composition comprising one or more active agents and optionally, one or more auxiliary ingredients, for example one or more structurants and/or one or more fillers; and b. producing a consumable, single use 3D article, for example a consumable, single use, water-insoluble 3D article from the 3D article-forming composition;

wherein the consumable, single use 3D article exhibits a Surface Area to Volume Ratio of greater than about 0.10 and/or greater than about 0.20 and/or greater than about 0.30 and/or greater than about 0.40 and/or greater than about 0.50 and/or greater than about 0.60 and/or greater than about 0.70 and/or greater than about 0.80 and/or greater than about 0.90 and/or greater than about 1.00 mm$^{-1}$ as measured according to the μCT Test Method; and wherein the consumable, single use 3D article exhibits a 3D Article Free Melt Flow of greater than about 20% as measured according to the 3D Article Free Melt Flow Test Method, is provided.

In yet another example of the present invention, a package comprising one or more consumable, single use 3D articles according to the present invention, is provided.

In even yet another example of the present invention, a method for treating surfaces, for example fabrics in need of treatment and/or hair in need of treatment, wherein the method comprises contacting one or more fabrics and/or hair with one or more consumable, single use 3D articles according to the present invention such that the fabrics and/or hair are treated, is provided.

The present invention provides consumable, single use 3D articles, methods for making same, packages containing same, and method for treating surfaces, for example fabric surfaces and/or hair surfaces, with such consumable, single use 3D articles.

Accordingly, the present invention provides active agent-containing 3D articles, for example consumable, single use active agent-containing 3D articles useful for treating fabrics and/or hair, methods for making same, and methods for treating surfaces, such as fabrics and/or hair with such 3D articles.

DETAILED DESCRIPTION OF THE INVENTION

Figure 1:
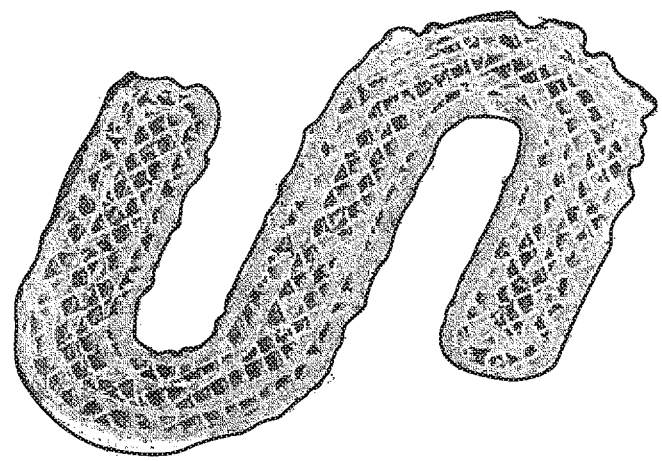
FIG. 1 is an image of an example of a 3D article according to the present invention, which in this case is a 3D printed 3D article.
Figure 2:
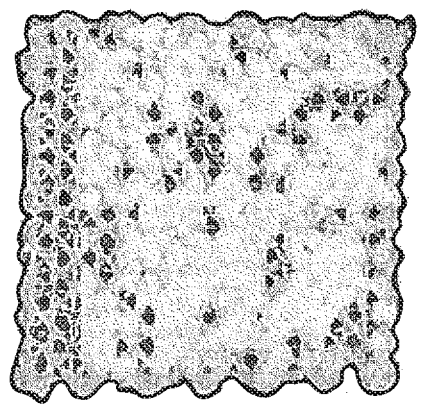
FIG. 2 is an image of another example of a 3D article according to the present invention, which in this case is a 3D printed 3D article.
Figure 3:
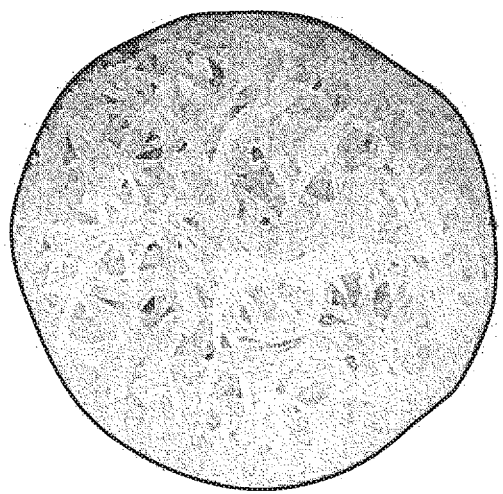
FIG. 3 is an image of another example of a 3D article according to the present invention, which in this case is an extruded 3D article.

"3D Article" as used herein refers to a 3D consumer use unit, a 3D consumer unit dose unit, a 3D consumer use saleable unit, or a 3D single dose unit. The 3D articles of the present invention may be homogeneous, heterogeneous or may be layered. If layered, the 3D articles may comprise at least two and/or at least three and/or at least four and/or at least five layers "3D Article-forming composition" as used herein means a composition, for example a non-aqueous composition and/or a substantially free of water composition that is suitable for making a 3D article of the present invention such as by 3D printing and/or extrusion. The 3D article-forming composition comprises one or more active agents suitable for printing and/or extruding into a 3D article. In addition to the one or more active agents, the 3D article-forming composition may comprise one or more auxiliary ingredients, such as one or more 3D article-forming materials, for example one or more structurants, that exhibit properties that make them suitable for printing and/or extruding into a 3D article. In one example, the auxiliary ingredients comprise one or more structurants, such as one or more polymers. In one example, the auxiliary ingredients comprise one or more fillers, such as one or more organic or inorganic particles.

In one example, the 3D article-forming composition may be made by heating and optionally stirring one or more active agents until the melted active agents are homogeneous. Then the homogeneous melted active agents, which in this case is the 3D article-forming composition, can be printed and/or extruded into 3D articles of the present invention. Alternatively, one or more auxiliary ingredients, such as 3D article-forming materials, for example structurants, such as polymeric structurants and/or inorganic structurants, may be added, with or without stirring and/or agitation, to the homogeneous melted active agents and dissolved, for example homogeneously dissolved, in and/or dispersed, for example homogeneously dispersed, throughout the melted active agents to form the 3D article-forming composition, which can then be printed and/or extruded into 3D articles of the present invention.

In one example, a 3D article of the present invention made from a 3D article-forming composition of the present invention is such that one or more active agents may be present in the 3D article rather than on the 3D article, such as a coating composition comprising one or more active agents, which may be the same or different from the active agents in the 3D article. The total level of 3D article-forming materials and total level of active agents present in the 3D article-forming composition may be any suitable amount so long as the 3D articles of the present invention are produced therefrom.

In one example, one or more active agents may be present in the 3D article and one or more additional active agents may be present on a surface of the 3D article as a coating. In another example, a 3D article of the present invention may comprise one or more active agents that are present in the 3D article when originally made, but then bloom to a surface of the 3D article prior to and/or when exposed to conditions of intended use of the 3D article.

"3D article-forming material" as used herein means a material, for example an auxiliary ingredient, such as a structurant, for example a polymer, a filler, and mixtures thereof, that exhibits properties suitable for making a 3D article.

"Active agent-containing particle" as used herein means a solid additive comprising one or more active agents. In one example, the active agent-containing particle is an active agent in the form of a particle (in other words, the particle comprises 100% active agent(s)). The active agent-containing particle may exhibit a median particle size of 2000 μm or less as measured according to the Median Particle Size Test Method described herein. In another example, the active agent-containing particle exhibits a median particle size of from about 1 μm to about 2000 μm and/or from about 1 μm to about 800 μm and/or from about 5 μm to about 500 μm and/or from about 10 μm to about 300 μm and/or from about 10 μm to about 100 μm and/or from about 10 μm to about 50 μm and/or from about 10 μm to about 30 μm as measured according to the Median Particle Size Test Method described herein. In one example, one or more of the active agents is in the form of a particle that exhibits a median particle size of 20 μm or less as measured according to the Median Particle Size Test Method described herein.

"Additive" as used herein means any material present in the 3D article of the present invention that is not a 3D article-forming material nor an active agent. In one example, an additive comprises a processing aid.

In another example, an additive may comprise a plasticizer for the 3D article. Non-limiting examples of suitable plasticizers for the present invention include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexanediol, 2,2,4-trimethylpentane-1,3-diol, and polyethylene glycol (200-600).

In yet another example, an additive may comprise one or more colors and/or dyes that are incorporated into the 3D articles of the present invention to provide a visual signal when the 3D articles are exposed to conditions of intended use and/or when an active agent is released from the 3D articles and/or when the 3D articles' morphology changes.

In even still yet another example, an additive may comprise one or more anti-blocking and/or detackifying agents. Non-limiting examples of suitable anti-blocking and/or detackifying agents include starches, starch derivatives, crosslinked polyvinylpyrrolidone, crosslinked cellulose, microcrystalline cellulose, silica, metallic oxides, calcium carbonate, talc, mica, and mixtures thereof.

"Conditions of intended use" as used herein means the temperature, physical, chemical, and/or mechanical conditions that a 3D article of the present invention is exposed to when the 3D article is used for one or more of its designed purposes. For example, if a 3D article of the present invention is designed to be used in an automatic clothes dryer and/or in a washing machine for laundry care purposes, the conditions of intended use will include those temperature, chemical, physical and/or mechanical conditions present in an automatic clothes dryer's clothes drying and/or conditioning operation and/or in a washing machine wherein the water-insoluble 3D article may form a lamellar structure as measured by the Lamellar Structure Test Method described herein. In another example, if a 3D article of the present invention is designed to be used by a human as a shampoo and/or conditioner for hair care purposes, the conditions of intended use will include those temperature, chemical, physical and/or mechanical conditions present during the shampooing and/or conditioning of the human's hair.

"Active agent" as used herein means a material that produces an intended effect in an environment external to a 3D article of the present invention, such as when the 3D article is exposed to conditions of intended use of the 3D article. In one example, an active agent comprises a material that treats a surface, such as a soft surface (i.e., fabric, hair, skin).

"Treats" as used herein with respect to treating a surface means that the active agent provides a benefit to a surface or environment. Treats includes regulating and/or immediately improving a surface's or environment's appearance, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g., building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair. Treats may include providing a benefit to fabrics like during a cleaning or softening in a laundry machine, providing a benefit to hair like during shampooing, conditioning, or coloring of hair, or providing a benefit to environments like a toilet bowl by cleaning or disinfecting it.

In another example, treating means removing stains and/or odors from fabric articles, such as clothes, towels, and linens.

"Fabric care active agent" as used herein means an active agent that when applied to a fabric provides a benefit and/or improvement to the fabric. Non-limiting examples of benefits and/or improvements to a fabric include conditioning, including softening, cleaning (for example by surfactants), stain removal, stain reduction, wrinkle removal, color restoration, static control, wrinkle resistance, permanent press, wear reduction, wear resistance, pill removal, pill resistance, soil removal, soil resistance (including soil release), shape retention, shrinkage reduction, softness, fragrance, anti-bacterial, anti-viral, odor resistance, and odor removal.

"Keratinous tissue active agent" as used herein means an active agent that may be useful for treating keratinous tissue (e.g., hair, skin, or nails) condition. For a hair care active agent, "treating" or "treatment" or "treat" includes regulating and/or immediately improving keratinous tissue cosmetic appearance and/or feel. For instance, "regulating skin, hair, or nail condition" includes: thickening of skin, hair, or nails (e.g., building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair. Another example of keratinous tissue active agent may be an active agent used in the shampooing, conditioning, or dyeing of hair.

"Weight ratio" as used herein means the ratio between two materials on their dry basis. For example, the weight ratio of 3D article-forming materials to active agents within a 3D article is the ratio of the weight of 3D article-forming material on a dry weight basis (g or %) in the 3D article to the weight of additive, such as active agent(s) on a dry weight basis (g or %—same units as the 3D article-forming material weight) in the 3D article.

"Water-insoluble" with respect to a 3D article and/or material as used herein means a 3D article and/or material of the present invention that does not dissolve in excess water and/or is not miscible in water. In other words, a water-insoluble article when subjected to agitation in excess water may break apart into pieces of the 3D article, but the pieces remain intact in the water. In another example, the 3D article is still water-insoluble even if the 3D article or pieces of the 3D article swell in the excess water so long as the 3D article and/or pieces of the 3D article remain intact. In one example, a 3D article and/or materials that exhibit a lamellar structure as determined according to the Lamellar Structure Test Method are considered water-insoluble herein.

In one example, the 3D article is water-insoluble. As defined herein, water-insoluble means that the 3D article does not completely dissolve or disintegrate when in contact with moisture from the laundered fabrics in the automatic drying process or when in contact with the aqueous wash/rinse bath of the washing process. Where the 3D articles are designed for use in the dryer, water-insoluble auxiliary ingredients, when present, are used instead of water-soluble auxiliary ingredients because water-soluble auxiliary ingredients, which dissolve and/or disintegrate in the presence of water, have the potential to stain or otherwise damage any fabrics being dried in the presence of the 3D articles when they contact a fabric.

"Ambient conditions" as used herein means 23° C.±1.0° C. and a relative humidity of 50%±2%.

"Weight average molecular weight" as used herein means the weight average molecular weight as determined using the industry standard method, gel permeation chromatography.

"3D Article dimensions," as used herein, refers to the surface area, volume, mass, surface area to volume ratio, bounding box volume, and bounding box density of a 3D article all of which are measured according to the μCT Test Method described herein.

"Surface Area to Volume Ratio" as used herein with respect to a 3D article means the Surface Area of the 3D article in units of $mm^2$ divided by the Volume of the 3D article in units of $mm^3$, thus resulting in the Surface Area to Volume Ratio having units of $mm^{-1}$. In one example, the 3D articles of the present invention exhibits a Surface Area to Volume Ratio of greater than about 0.10 and/or greater than about 0.20 and/or greater than about 0.30 and/or greater than about 0.40 and/or greater than about 0.50 and/or greater than about 0.60 and/or greater than about 0.70 and/or greater than about 0.80 and/or greater than about 0.90 and/or greater than about 1.00 and/or less than about 1,000 and/or less than about 700 and/or less than about 500 and/or less than about 300 and/or less than about 100 and/or less than about 50 and/or less than about 25 and/or less than about 10 $mm^{-1}$ as measured according to the μCT Test Method. In another example, the 3D articles of the present invention exhibit a Surface Area to Volume Ratio of from about 0.10 to about 1,000 and/or from about 0.30 to about 500 and/or from about 0.50 to about 300 and/or from about 0.70 to about 100 and/or from about 0.90 to about 50 and/or from about 0.90 to about 25 and/or from about 1.00 to about 10 $mm^{-1}$ as measured according to the μCT Test Method.

"Mass," as used herein with respect to a 3D article, may refer to the measurement according to its conventional definition. For example, the mass of a 3D article can be measured using a top loading analytical balance with a resolution of ±0.01 g, where the balance is protected from air drafts and other disturbances by a draft shield. After conditioning the 3D article, the mass of the 3D article can be measured to the nearest 0.01 g. In one example, an average mass can be provided by measuring ten substantially similar replicate articles, compiling an average of the ten individual article mass measurements, and reporting the value to the nearest 0.01 g. The mass of a 3D article, for example, can be measured according to the Mass Test Method described herein.

"Triggering condition" as used herein in one example means anything, as an act or event, that serves as a stimulus and initiates or precipitates a change in the 3D article or portion of the 3D article of the present invention, such as a loss or altering of the 3D article's physical structure and/or a release of an active agent therefrom. In another example, the triggering condition may be present in an environment, such as heat within an automatic clothes dryer, when a 3D article of the present invention is added to the automatic clothes dryer and/or when added to a wash liquor, such as water and optionally detergent, with fabrics, for example in a washing machine wherein the water-insoluble article may form a lamellar structure as measured by the Lamellar Structure Test Method described herein.

3D Article

The 3D articles of the present invention may comprise a plurality of active agents. In one example, the total level of the one or more active agents present in the 3D articles of the present invention is 80% or greater and/or greater than 85% and/or greater than 90% and/or greater than 95% and/or greater than 96% and/or greater than 97% and/or greater than 98% and/or greater than 99% and/or about 100% by weight on a dry 3D article basis. In one example, the total level of the one or more active agents present in the 3D articles of the present invention is greater than 30% and/or greater than 40% and/or greater than 50% and/or greater than 60% and/or greater than 70% and/or greater than 80% and/or greater than 90% and/or greater than 95% and/or greater than 96% and/or greater than 97% and/or greater than 98% and/or greater than 99% and/or about 100% by weight on a dry 3D article basis. In one example, one or more auxiliary ingredients, for example one or more 3D article-forming materials, such as one or more structurants, may be present in the 3D articles at a total level of 20% or less and/or less than 15% and/or less than 10% and/or less than 5% and/or less than 4% and/or less than 3% and/or less than 2% and/or less than 1% and/or about 0% by weight on a dry 3D article basis. In another example, one or more auxiliary ingredients, for example one or more 3D article-forming materials, such as one or more fillers, may be present in the 3D articles at a total level of 60% or less and/or less than 40% and/or less than 30% and/or less than 20% and/or less than 15% and/or less than 10% and/or less than 5% and/or less than 2% and/or about 0% by weight on a dry 3D article basis.

In one example, one or more active agents may be uniformly distributed or substantially uniformly distributed throughout the 3D article. In another example, one or more active agents may be distributed as discrete regions within the 3D article. In still another example, at least one active agent is distributed uniformly or substantially uniformly throughout the 3D article and at least one other active agent is distributed as one or more discrete regions within the 3D article. In still yet another example, at least one active agent is distributed as one or more discrete regions within the 3D article and at least one other active agent is distributed as one or more discrete regions different from the first discrete regions within the 3D article.

Without wishing to be bound by theory, it is believed that 3D article dimensions can contribute to achieving the most consumer-preferred combination of performance factors of the 3D article, with such factors including consumer-preferred 3D article flexibility and containment or dispensing. In one example, the 3D article of the present invention is a standalone entity ready for use and a collection and/or number of these entities may be distributed to consumers in a product-shipping assembly, for example a protective product-shipping assembly.

Furthermore, it is believed that 3D article dimensions can contribute to achieving a product-shipping assembly that can provide desirable packaging properties, such as minimized packaging sizes, reduced shipping costs, and a maximized ratio of a 3D article volume to a packaging volume, while still providing sufficient protection for the 3D articles. For example, it is believed that providing desirable 3D article dimensions can facilitate reduction of dunnage, thereby reducing costs and waste; improve efficiency in shipping by, for example, providing a shipping container that can fit in a mail slot; and ensure sufficient immobilization and protection of the 3D articles by, for example, minimizing the space in which the 3D article can move within the shipping container.

The 3D article can have a surface area of greater than about 100 and/or greater than about 500 and/or greater than about 1,000 and/or greater than about 3,000 and/or greater than about 5,000 and/or greater than about 7,000 and/or less than about 1,500,000 and/or less than about 1,000,000 and/or less than about 500,000 and/or less than about 300,000 and/or less than about 100,000 and/or less than about 50,000 and/or less than about 25,000 mm² as measured according to the μCT Test Method described herein. In certain examples, the 3D article can have a surface area of greater than about 100 to about 1,500,000 and/or from about 500 to about 500,000 and/or from about 1,000 to about 100,000 and/or from about 3,000 to about 50,000 and/or from about 5,000 to about 25,000 and/or from about 5,000 to about 15,000 and/or from about 5,000 to about 10,500 mm² as measured according to the μCT Test Method described herein.

The 3D article can have a volume of greater than about 50 and/or greater than about 100 and/or greater than about 200 and/or greater than about 300 and/or greater than about 400 and/or greater than about 500 and/or greater than about 600 and/or greater than about 700 and/or greater than about 800 and/or greater than about 900 and/or greater than about 1,000 and/or less than about 1,250,000 and/or less than about 500,000 and/or less than about 375,000 and/or less than about 250,000 and/or less than about 200,000 and/or less than about 150,000 and/or less than about 125,000 and/or less than about 100,000 and/or less than about 75,000 and/or less than about 50,000 and/or less than about 40,000 mm³ as measured according to the μCT Test Method described herein. In certain examples, the 3D article can have a volume of from about 50 to about 1,250,000 and/or from about 100 to about 500,000 and/or from about 500 to about 150,000 and/or from about 900 to about 50,000 and/or from about 1,000 to about 40,000 cm³ as measured according to the μCT Test Method described herein.

In one example, the 3D articles according to the present invention may exhibit a mass of less than 125 g and/or less than 100 g and/or greater than 0.01 g and/or greater than 0.1 g and/or greater than 0.2 g and/or greater than 0.5 g as measured according to the Mass Test Method described herein. In one example, the 3D articles according to the present invention may exhibit a mass of from about 0.01 to about 125 g and/or from about 0.1 to about 100 g and/or from about 0.2 to about 75 g and/or from about 0.3 to about 50 g and/or from about 0.4 to about 40 g and/or from about 0.5 to about 30 g and/or from about 0.6 to about 25 g and/or from about 0.7 to about 20 g and/or from about 0.8 to about 15 g and/or from about 0.9 to about 10 g and/or from about 1 to about 8 g as measure according to the Mass Test Method described herein.

The 3D article can have a bounding box density of greater than about 0.01 g/cc ("g/cm³") and/or greater than about 0.02 g/cc and/or greater than 0.05 g/cc and/or greater than about 0.08 g/cc and/or greater than about 0.09 g/cc and/or greater than about 0.10 g/cc and/or greater than about 0.13 g/cc and/or greater than about 0.15 g/cc and/or greater than about 0.20 g/cc or less than about 0.98 g/cc and/or less than about 0.95 g/cc and/or less than about 0.80 g/cc and/or less than about 0.70 g/cc and/or less than about 0.60 g/cc and/or less than about 0.55 g/cc and/or less than about 0.50 g/cc and/or less than about 0.40 g/cc and/or less than about 0.35 g/cc as measured according to the μCT Test Method described herein. In certain examples, the 3D article can have a bounding box density of greater than about 0.01 g/cc to about 0.98 g/cc and/or greater than about 0.01 g/cc to about 0.95 g/cc and/or greater than about 0.05 g/cc to about 0.70 g/cc and/or greater than about 0.09 g/cc to about 0.55 g/cc greater than about 0.15 g/cc to about 0.40 g/cc and/or greater than about 0.20 g/cc to about 0.35 g/cc as measured according to the μCT Test Method described herein.

The 3D article can have a bounding box volume of greater than about 100 and/or greater than about 250 and/or greater than about 500 and/or greater than about 750 and/or greater than about 1,000 and/or greater than about 3,000 and/or greater than about 5,000 and/or greater than about 7,000 and/or less than about 1,500,000 and/or less than about 1,000,000 and/or less than about 500,000 and/or less than about 300,000 and/or less than about 100,000 and/or less than about 50,000 and/or less than about 25,000 and/or less than 10,000 mm³ as measured according to the μCT Test Method described herein. In certain examples, the 3D article can have a surface area of greater than about 100 to about 1,500,000 and/or from about 250 to about 500,000 and/or from about 5000 to about 100,000 and/or from about 500 to about 50,000 and/or from about 750 to about 25,000 and/or from about 1,000 to about 15,000 and/or from about 1,000 to about 10,000 mm³ as measured according to the μCT Test Method described herein.

In certain examples, the 3D article has one or more and/or two or more and/or three or more and/or four or more and/or five or more and/or all six of the 3D article dimensions described herein as measured according to the μCT Test Method described herein.

A product-shipping assembly can include a plurality of 3D articles. In certain examples, each 3D article can include one or more active agents releasable from the 3D articles, and optionally one or more 3D article-forming materials. Each of the plurality of 3D articles can have 3D article dimensions in accordance to those described herein. The product-shipping assembly can further include a shipping container defining an internal volume sized to removably contain the product. In one example, the product-shipping assembly exhibits a ratio of volume of the plurality of articles to the internal volume is about 0.8 or greater.

In certain examples, the product-shipping assembly can further include a support member. In certain examples, the support member can be in contact with the product, and in some examples, the support member can be attached to the product. The support member can support one or more of the plurality of 3D articles and/or facilitate the securement thereof within the shipping container. In one example, the support member can be a tray, where the tray can be sized to fit within the shipping container, such that the plurality of 3D articles may be slidably removed from the shipping container while being substantially contained within the tray. It will be appreciated, however, that a support member may be provided in any of a variety of suitable configurations. The product-shipping assembly may further include one or more dividers, wherein the one or more dividers separate the plurality of 3D articles. In certain examples, the one or more dividers can provide boundaries between multiple compartments within the shipping container, where the plurality of 3D articles can be divided between the multiple compartments, separated by the one or more dividers.

In certain examples, the product-shipping assembly may include a barrier to humidity, liquids (e.g., water), and scent escape. In certain examples, the shipping container can include a protective coating applied to an interior of the shipping container, where the protective coating can serve as the barrier. In one example, the protective coating can be a thin polymeric film. However, it will be appreciated that a protective coating can be any of a variety of suitable coatings known in the art, and the protective coating may be applied through any conventional coating methods known in the art. In certain examples, the protective coating can define the internal volume of the shipping container or be included within the internal volume of the shipping container. The protective coating can be water impermeable, water vapor resistant, and/or scent impermeable.

In other examples, the product-shipping assembly can include one or more overwraps, where the one or more overwraps can serve as the barrier. In certain examples, the one or more overwraps can fully or at least partially wrap an exterior of the shipping container. In certain examples, the one or more overwraps can fully or at least partially cover or surround one or more articles of the plurality of 3D articles. In certain examples, the one or more overwraps can further serve to facilitate the securement of the plurality of 3D articles within the shipping container. In one example, the one or more overwraps can substantially wrap each article, and the overwrap may seal the 3D article therein. The one or more overwraps may be a shrink wrap, a film wrap, a paper wrap, and/or any of a variety of other suitable wraps. Like the protective coating, in certain examples, the one or more overwraps can be water impermeable, water vapor resistant, and/or scent impermeable.

In certain examples, the product-shipping assembly can further include a vent. The vent can allow for off-gassing of, for example, one or more scents, carbon dioxide, oxygen, water vapor, or other gases from the product-shipping assembly. In one example, the vent may include one or more apertures in, for example, a shipping container and/or one or more overwraps.

In certain examples, however, the product-shipping assembly may be substantially dunnage-free, such that the product-shipping assembly may include minimal excessive protective packaging materials, such as bubble wrap, Styrofoam, and the like, or be completely free thereof. In one example, a ratio of a volume of the plurality of 3D articles to the internal volume can be about 0.8 or greater. In certain examples, the ratio of the volume of the plurality of 3D articles to the internal volume can be about 0.85 or greater; about 0.9 or greater; or about 0.95 or greater.

The shipping container can be any package, box, carton, bag, wrap, or other conventional type of receptacle used in the packing and distribution of products, as described above. The shipping container can be suitable for use in e-commerce. In one example, the shipping container can have a width of about 6 inches or less; a length of about 10 inches or less; and a height of about 1.75 inches or less. In such an example, the shipping container may be sized and shaped to fit into a conventional mail slot. It will be appreciated, however, that a shipping container can be provided in any of a variety of suitable sizes, shapes, and configurations.

The plurality of 3D articles may include from about 2 articles to about 144 articles, and any amount of 3D articles in between. For example, the plurality of 3D articles can include about 2 articles or more; about 8 articles or more; about 12 articles or more; about 18 articles or more; about 24 articles or more; about 25 articles or more; about 30 articles or more; about 36 articles or more; about 40 articles or more; about 48 articles or more; about 50 articles or more; about 60 articles or more; or about 64 articles or more. In certain examples, at least two articles of the plurality of 3D articles can have different scents.

The product-shipping assembly can further include a water scavenging material. In one example, the water scavenging material can be a desiccant. However, it will be appreciated that the water scavenging material can be any of a variety of suitable water scavenging materials known in the art.

In one example, the 3D article may comprise two or more regions or layers that comprise different active agents. For example, one region of the 3D article may comprise anti-static agents and another region of the 3D article may comprise fabric conditioning agents.

With respect to the 3D articles of the present invention, they are in solid form at ambient conditions prior to use. However, the 3D article-forming composition used to make the 3D articles of the present invention may be in the form of a liquid.

In one example, the 3D article may comprise different active agents. This may be the case where the different active agents may be incompatible with one another, for example a cationic surfactant (such as a hair conditioner active agent).

In another example, the 3D article may exhibit different regions, such as different regions of basis weight, density and/or caliper. In yet another example, the 3D article may comprise texture on one or more of its surfaces. A surface of the 3D article may comprise a pattern, such as a non-random, repeating pattern. In another example, the 3D article may comprise apertures and/or holes and/or voids. The apertures and/or holes and/or voids may be arranged in a non-random, repeating pattern.

The 3D article of the present invention may be used as is or may be coated with one or more active agents.

The 3D articles of the present invention may exhibit one or more of the following properties.

In one example, the 3D articles of the present invention may exhibit a lamellar structure upon wetting as determined by the Lamellar Structure Test Method described herein.

In one example, the 3D articles of the present invention may exhibit a lamellar structure upon wetting as determined by the Lamellar Structure Test Method described herein, but does not exhibit a lamellar structure in a conditioned only, dry state as determined by the Lamellar Structure Test Method.

In one example, the 3D articles of the present invention may exhibit an Air Permeability of at least 20 and/or at least 40 and/or at least 60 and/or at least 80 and/or less than 7000 and/or less than 6000 and/or less than 5000 and/or less than 4000 and/or less than 3000 and/or less than 2000 $L/m^2/s$ as measured according to the Air Permeability Test Method described herein.

In one example, the 3D articles of the present invention may exhibit a Free Melt Flow of greater than about 20% and/or greater than about 30% and/or greater than about 40% and/or greater than about 50% and/or greater than about 60% and/or greater than about 70% and/or greater than about 80% and/or greater than about 85% and/or greater than about 90% and/or greater than about 95% and/or greater than about 97% and/or greater than about 98% and/or greater than about 99% and/or about 100% as measured according to the Free Melt Flow Test Method described herein.

In one example, the 3D article exhibits a water content of from about 0% to about 20% and/or from about 0% to about 5% as measured according to the Water Content Test Method. In one example, the 3D article exhibits a water content of from about 2% to about 15% and/or from about 2% to about 10% and/or from about 5% to about 10% as measured according to the Water Content Test Method.

In one example, the 3D article comprises adhesive or a material that functions as an adhesive, for example on one or more surfaces of the 3D article to attach the 3D article to an automatic clothes dryer internal drum surface.

In one example, during use of the 3D article in an automatic clothes dryer operation, the 3D article transfers (deposits) at least a portion, and/or substantially all of its mass to fabrics being treated, for example dried and/or conditioned, in the automatic clothes dryer.

In one example, during use of the 3D article in a washing machine operation, the 3D article transfers (deposits) at least a portion, and/or substantially all of its mass to fabrics being treated, for example washed and/or conditioned, in the washing machine.

Active Agents

Non-limiting examples of suitable active agents for use in the fibrous elements and/or films and/or articles of the present invention include dryer-added active agents, such as fabric conditioning active agents, and/or hair care conditioning active agents. As used herein a "fabric conditioning active agent" means any material that performs a function or delivers a benefit, such as modifying the physical or chemical properties of a treated material (e.g., fabric). Even though the description relates primarily to treating fabrics, the fabric conditioning active agents may also provide benefits, such as conditioning benefits to hair (e.g., hair conditioning active agents).

Non-limiting examples of suitable fabric conditioning active agents and/or hair conditioning active agents include: perfumes, fabric conditioning agents, anti-static agents, crisping agents, water/stain repellents, stain release agents, refreshing agents, disinfecting agents, wrinkle resistance agents, wrinkle release agents, odor resistance agents, malodor control agents, abrasion resistance and protection agents, solvents, insect/pet repellents, wetting agents, UV protection agents, skin/fabric conditioning agents, skin/fabric nurturing agents, skin/fabric hydrating agents, color protection agents, dye fixatives, dye transfer inhibiting agents, silicones, preservatives and anti-microbials, fabric shrinkage-reducing agents, brighteners, hueing dyes, bleaches, chelants, antifoams, anti-scum agents, whitening agents, catalysts, cyclodextrin, zeolite, petrolatum, glycerin, triglycerides, vitamins, other skin care actives such as aloe vera, chamomile, shea butter and the like, mineral oils, and mixtures thereof. In one example, the articles of the present invention comprise one or more fabric conditioning active agents for imparting one or more fabric care benefits such as softening, anti-static, color protection, etc., to fabrics. In another example, the articles of the present invention may comprise one or more fabric conditioning active agents selected from the group consisting of: perfumes, builders, chelants, antioxidants, brighteners, sun fade inhibiting agents, UV absorbing agents, insect repellants, scents, bleaching agents, enzymes, antimicrobials, antibacterials, antifungals, perfume delivery systems, perfume microcapsules, dye transfer inhibiting agents, hueing dyes, soil release agents, such as soil release polymers, for example soil release polymer that comprise copolymeric blocks of terephthalate and polyethylene oxide or polypropylene oxide, and cationic soil release agents, colorants, preservatives, opacifiers, stabilizers such as guar gum and polyethylene glycol, anti-shrinkage agents, anti-wrinkle agents, soil release agents, fabric crisping agents, reductive agents, spotting agents, germicides, fungicides, anti-corrosion agents, and mixtures thereof. In one example, the articles of the present invention comprise one or more hair conditioning active agents for imparting one or more hair care benefits such as softening, anti-static, color protection, etc. to hair.

In one example, the articles of the present invention comprise one or more fabric conditioning active agents and/or hair conditioning active agents selected from the group consisting of: fatty fabric conditioning active agents (for example fatty acids and/or fatty acid derivatives and/or fatty alcohols), sulfonic acid derivatives, quaternary ammonium compounds, tertiary amines and salts thereof, nonionic surfactants, and mixtures thereof.

In one example, the fabric conditioning active agent and/or hair conditioning active agents comprises, alone or in combination with one or more fatty fabric conditioning active agents and/or fatty hair conditioning active agents (for example one or more fatty acids and/or one or more fatty alcohols), one or more quaternary ammonium compounds selected from the group consisting of: di(tallowyloxyethyl)hydroxyethylmethylammoniummethylsulfate, dimethyl bis(stearoyl oxyethyl)ammonium chloride, dimethyl bis(tallowyloxyethyl)ammonium chloride, dimethyl bis(tallowyloxyisopropyl)ammonium methylsulfate and mixtures thereof.

In one example, the fabric conditioning active agent and/or hair conditioning active agent comprises, alone or in combination with one or more quaternary ammonium compounds and/or one or more fatty alcohols, one or more fatty acids selected from the group consisting of: myristic acid, stearic acid, isostearic acid, cetearic acid, dodecanoic acid, linoleic acid, oleic acid, palmitic acid, lauric acid, and mixtures thereof.

In one example, the fabric conditioning active agent and/or hair conditioning active agent comprises, alone or in combination with one or more quaternary ammonium compounds and/or one or more fatty acids, one or more fatty alcohols selected from the group consisting of: cetyl alcohol, stearyl alcohol, behenyl alcohol, lauryl alcohol, myristic alcohol, isostearyl alcohol, arachidyl alcohol, and mixtures thereof.

Quaternary Ammonium Compounds

In one example, the fabric conditioning active agent and/or hair conditioning active agents comprises one or more fatty alcohols and one or more quaternary ammonium compounds. In one example, the article of the present invention comprises one or more fatty alcohols and one or more quaternary ammonium compounds in a weight ratio of greater than 1:1 and/or greater than 1.5:1 and/or greater than 1.75:1 and/or greater than 1.9:1.

In one example, the fabric conditioning active agent and/or hair conditioning active agent comprises one or more fatty acids and one or more quaternary ammonium compounds. In one example, the article of the present invention comprises one or more fatty acids and one or more quaternary ammonium compounds in a weight ratio of greater than 1:1 and/or greater than 1.5:1 and/or greater than 1.75:1 and/or greater than 1.9:1.

In one example, the fabric conditioning active agent and/or hair conditioning active agent comprises a quaternary ammonium compound. Non-limiting examples of quaternary ammonium compounds include alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. See U.S. Patent Pub. 2005/0192207 at 57-66. The fabric conditioning active agents and/or hair conditioning active agents can be one or a mixture of a quaternary ammonium compound, a tertiary amine and or its salts, an ethoxylated fatty material, a fatty acid or a mixture thereof. Non-limiting examples of fabric conditioning active agents that are especially useful in the articles of the present invention are described in U.S. Pat. No. 4,103,047, Zaki et al., issued Jul. 25, 1978; U.S. Pat. No. 4,237,155, Kardouche, issued Dec. 2, 1980; U.S. Pat. No. 3,686,025, Morton, issued Aug. 22, 1972; U.S. Pat. No. 3,849,435, Diery et al., issued Nov. 19, 1974: and U.S. Pat. No. 4,073,996, Bedenk, issued Feb. 14, 1978; said patents are hereby incorporated herein by reference. Other fabric conditioning active agents and/or hair conditioning active agents are disclosed hereinafter.

Non-limiting examples of suitable quaternary ammonium compounds include cationic fabric conditioning active agents and/or cationic hair conditioning active agents and their salts such as dialkyl dimethylammonium chlorides, methylsulfates and ethylsulfates wherein the alkyl groups can be the same or different and contain from about 12 to about 22 carbon atoms. Non-limiting examples of such cationic fabric conditioning active agents and/or cationic hair conditioning active agents include ditallowalkyldimethylammonium methylsulfate (DTDMAMS), distearyldimethylammonium methylsulfate, dipalmityldimethylammonium methylsulfate and dibehenyldimethylammonium methylsulfate.

Another example of a suitable fabric conditioning active agent and/or hair conditioning active agents is an ester quaternary ammonium compound (EQA) selected from Formulas IA, IB, II, III, IV, and mixtures thereof.

Formula IA comprises:

wherein each Y=—O—(O)C—, or —C(O)—O—; p=1 to 3; each v=is an integer from 1 to 4, and mixtures thereof; each $R^1$ substituent is a short chain $C_1$-$C_6$, and/or $C_1$-$C_3$, alkyl group, e.g., methyl, ethyl, propyl, and the like, benzyl and mixtures thereof; each $R^2$ is a long chain, saturated and/or unsaturated (Iodine Value of from about 3 to about 60), $C_8$-$C_{30}$ hydrocarbyl, or substituted hydrocarbyl substituent and mixtures thereof; and the counterion, $X^-$, can be any softener-compatible anion, for example, methylsulfate, ethylsulfate, chloride, bromide, formate, sulfate, lactate, nitrate, benzoate, and the like, such as methylsulfate.

It will be understood that substituents $R^1$ and $R^2$ of Formula IA can optionally be substituted with various groups such as alkoxyl or hydroxyl groups. In one example, Formula IA compounds are diester quaternary ammonium salts (DEQA). At least about 25% of the DEQA is in the diester form, and from 0% to about 40% and/or less than about 30% and/or less than about 20%, can be EQA monoester (e.g., only one —Y—$R^2$ group).

Formula IB comprises:

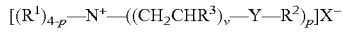

wherein each Y=—O—(O)C—, or —C(O)—O—; p=1 to 3; each v=is an integer from 1 to 4, and mixtures thereof; each $R^1$ substituent is a short chain $C_1$-$C_6$, and/or $C_1$-$C_3$, alkyl group, e.g., methyl, ethyl, propyl, and the like, benzyl and mixtures thereof; each $R^2$ is a long chain, saturated and/or unsaturated (Iodine Value of from about 3 to about 60), $C_8$-$C_{30}$ hydrocarbyl, or substituted hydrocarbyl substituent and mixtures thereof; each $R^3$ substituent is a short chain $C_1$-$C_6$ including benzyl, and/or $C_1$-$C_3$ alkyl group e.g., methyl, ethyl, propyl, and/or $C_1$-$C_2$ e.g., methyl, ethyl, and mixtures thereof; and the counterion, $X^-$, can be any softener-compatible anion, for example, methylsulfate, ethylsulfate, chloride, bromide, formate, sulfate, lactate, nitrate, benzoate, and the like, such as methylsulfate.

It will be understood that substituents $R^1$ and $R^2$ of Formula IB can optionally be substituted with various groups such as alkoxyl or hydroxyl groups. In one example, Formula IB compounds are diester quaternary ammonium salts (DEQA). At least about 25% of the DEQA is in the diester form, and from 0% to about 40% and/or less than about 30% and/or less than about 20%, can be EQA monoester (e.g., only one —Y—$R^2$ group).

As used herein, when the diester is specified, it will include the monoester that is normally present. For the optimal antistatic benefit the percentage of monoester should be as low as possible, such as less than about 2.5%. The level of monoester present can be controlled in the manufacturing of the EQA.

EQA compounds prepared with fully saturated acyl groups are excellent softeners. However, it has now been discovered that compounds prepared with at least partially unsaturated acyl groups have advantages (i.e., anti-static benefits) and are highly acceptable for consumer products when certain conditions are met. Variables that must be adjusted to obtain the benefits of using unsaturated acyl groups include the Iodine Value of the fatty acids, the odor of fatty acid starting material, and/or the EQA. Any reference to Iodine Value values hereinafter refers to Iodine Value of fatty acyl groups and not to the resulting EQA compound.

Some highly desirable, readily available sources of fatty acids such as tallow, possess odors that remain with the compound EQA despite the chemical and mechanical processing steps which convert the raw tallow to finished EQA. Such sources must be deodorized, e.g., by absorption, distillation (including stripping such as steam stripping), etc., as is well known in the art. In addition, care must be taken to minimize contact of the resulting fatty acyl groups to oxygen and/or bacteria by adding antioxidants, antibacterial agents, etc.

Generally, hydrogenation of fatty acids to reduce polyunsaturation and to lower Iodine Value to insure good color and odor stability leads to a high degree of trans configuration in the molecule. Therefore, diester compounds derived from fatty acyl groups having low Iodine Value values can be made by mixing fully hydrogenated fatty acid with touch hydrogenated fatty acid at a ratio which provides an Iodine Value of from about 3 to about 60. The polyunsaturation content of the touch hardened fatty acid should be less than about 5% and/or less than about 1%. During touch hardening the cis/trans isomer weight ratios are controlled by methods known in the art such as by optimal mixing, using specific catalysts, providing high $H_2$ availability, etc.

It has been found that a solvent may be used to facilitate processing of the Formula IA and/or IB EQA and/or of the fabric conditioning composition containing the EQA Formula IA and/or IB.

It has also been found that for good chemical stability of the diester quaternary compound in molten storage, water levels in the raw material must be minimized, for example to less than about 8% and/or less than about 5%. Storage temperatures should be kept as low as possible and still maintain a fluid material, ideally in the range of from about 45° C. to about 70° C. The optimum storage temperature for stability and fluidity depends on the specific Iodine Value of the fatty acid used to make the diester quaternary and the level/type of solvent selected. Also, exposure to oxygen should be minimized to keep the unsaturated groups from oxidizing. It can therefore be important to store the material under a reduced oxygen atmosphere such as a nitrogen blanket. It is important to provide good molten storage stability to provide a commercially feasible raw material that will not degrade noticeably in the normal transportation/storage/handling of the material in manufacturing operations.

The following are non-limiting examples of EQA Formula IA or IB (wherein all long-chain alkyl substituents are straight-chain):

Saturated $(C_2H_5)_2{}^+N(CH_2CH_2OC(O)C_{17}H_{35})_2$ $(CH_3SO_4)^-$(HO—CH(CH_3)CH_2)(CH_3)^+N(CH_2CH_2OC(O)C_{15}H_{31})_2Br^-$(CH_3)(C_2H_5)^+N(CH_2CH_2OC(O)C_{13}H_{27})_2$ $(HCOO)^-$(CH_3)_2{}^+N(CH_2CH(CH_3))OC(O)C_{18}H_{37})_2(CH_3SO_4)^-{}^+(C_3H_7)(C_2H_5)^+N(CH_2CH_2OC(O)C_{11}H_{23})_2 (CH_3SO_4)^-$

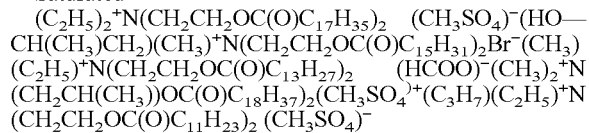

$(CH_3)_2{}^+N(CH_2CH_2OC(O)R^2)_2$ $(CH_3SO_4)^-$(CH_2CH_2OH)(CH_3)^+N(CH_2CH_2OC(O)R^2)_2 (CH_3SO_4)^-$
where —C(O)$R^2$ is derived from saturated tallow.

Unsaturated $(C_2H_5)_2{}^+N(CH_2CH_2OC(O)C_{17}H_{33})_2$ $(CH_3SO_4)^-$(HO—CH(CH_3)CH_2)(CH_3)^+N(CH_2CH_2OC(O)C_{15}H_{29})_2Br^-$(C_2H_5)_2{}^+N(CH_2CH_2OC(O)C_{17}H_{33})_2Cl^-$(CH_3)_2{}^-N(CH_2CH(CH_3))OC(O)C_{18}H_{35})_2(CH_3SO_4)^-$(CH_3)(C_2H_5)^+N(CH_2CH_2OC(O)C_{13}H_{27})_2 (C_6H_5COO)^-$

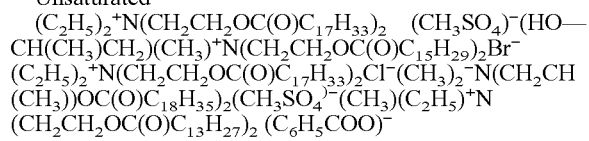

$(CH_2CH_2OH)(CH_3)^+N(CH_2CH_2OC(O)R^2)_2$ $(CH_3SO_4)^-$(CH_3)_2{}^+N(CH_2CH_2OC(O)R^2)_2$ $(CH_3SO_4)^-$(HOCH_2CH_2)(CH_3)N^+(CH_2CH_2OC(O)R^2)_2(CH_3SO_4)^-$
where —C(O)$R^2$ is derived from partially hydrogenated tallow or modified tallow having the characteristics set forth herein.

In addition to Formula IA and IB compounds, the compositions and articles of the present invention comprise EQA compounds of Formula II:

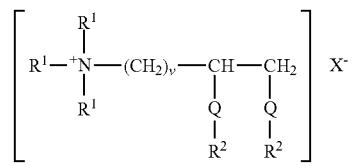

wherein, for any molecule: each Q is —O—C(O)— or —C(O)—O—; each $R^1$ is $C_1$-$C_4$ alkyl or hydroxy alkyl; $R^2$ and v are defined hereinbefore for Formula IA and IB; for example wherein $R^1$ is a methyl group, v is 1, Q is —O—C(O)—, each $R^2$ is $C_{14}$-$C_{18}$, and $X^-$ is methyl sulfate.

The straight or branched alkyl or alkenyl chains, $R^2$, have from about 8 to about 30 carbon atoms and/or from about 14 to about 18 carbon atoms and/or straight chains having from about 14 to about 18 carbon atoms.

Tallow is a convenient and inexpensive source of long chain alkyl and alkenyl materials.

A specific example of a Formula II EQA compound suitable for use as a fabric conditioning active agent and/or hair conditioning active agent herein is: 1,2-bis(tallowyloxy)-3-trimethyl ammoniopropane methylsulfate (DTT-MAPMS).

Other examples of suitable Formula II EQA compounds of this invention are obtained by, e.g., replacing "tallowyl" in the above compounds with, for example, cocoyl, lauryl, oleyl, stearyl, palmityl, or the like; replacing "methyl" in the above compounds with ethyl, propyl, isopropyl, butyl, isobutyl, t-butyl, or the hydroxy substituted analogs of these radicals; and/or replacing "methylsulfate" in the above compounds with chloride, ethylsulfate, bromide, formate, sulfate, lactate, nitrate, and the like, for example methylsulfate.

In addition to Formula IA and IB and Formula II compounds, the articles of the present invention may comprise EQA compounds of Formula III:

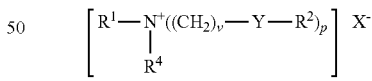

wherein $R^4$=a short chain $C_1$-$C_4$ alcohol; p is 2; $R^1$, $R^2$, v, Y, and $X^-$ are as previously defined for Formula IA and IB.

A specific example of a Formula III compound suitable for use as a fabric conditioning active agent and/or hair conditioning active agent herein is N-methyl-N,N-di-(2-($C_{14}$-$C_{18}$-acyloxy) ethyl), N-2-hydroxyethyl ammonium methylsulfate. An example of such as compound is N-methyl, N,N-di-(2-oleyloxyethyl) N-2-hydroxyethyl ammonium methylsulfate.

Fabric conditioning active agents and/or hair conditioning active agents of the present invention may also comprise Formula IV compounds:

wherein $R^1$, $R^2$, p, v, and $X^-$ are previously defined in Formula IA and IB; and

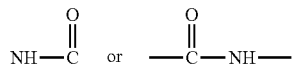

and mixtures thereof, wherein at least one Y" group is

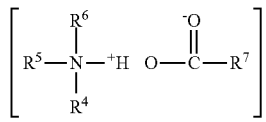

An example of this compound is methyl bis (oleyl amidoethyl) 2-hydroxyethyl ammonium methyl sulfate.

In one example, the fabric conditioning active agent and/or hair conditioning active agent of the present invention is a quaternary ammonium compound.

The compounds herein can be prepared by standard esterification and quaternization reactions, using readily available starting materials. General methods for preparation are disclosed in U.S. Pat. No. 4,137,180, which is incorporated herein by reference.

Tertiary Amines and Salts Thereof

Another fabric conditioning active agent and/or hair conditioning active agent useful in the fibrous elements and/or films and/or articles of the present invention is a carboxylic acid salt of a tertiary amine and/or ester amine having the formula:

$$\left[ \begin{array}{c} R^6 \\ | \\ R^5-N-{}^+H \quad O-\overset{\overset{\displaystyle O}{\|}}{C}-R^7 \\ | \\ R^4 \end{array} \right]$$

wherein $R^5$ is a long chain aliphatic group containing from about 8 to about 30 carbon atoms; $R^6$ and $R^4$ are the same or different from each other and are selected from the group consisting of aliphatic groups containing from about 1 to about 30 carbon atoms, hydroxyalkyl groups of the Formula $R^8OH$ wherein $R^8$ is an alkylene group of from about 2 to about 30 carbon atoms, and alkyl ether groups of the formula $R^9O(C_nH_{2n}O)_m$ wherein $R^9$ is alkyl and alkenyl of from about 1 to about 30 carbon atoms and hydrogen, n is 2 or 3, and m is from about 1 to about 30; wherein $R^4$, $R^5$, $R^6$, $R^8$, and $R^9$ chains can be ester interrupted groups; and wherein $R^7$ is selected from the group consisting of unsubstituted alkyl, alkenyl, aryl, alkaryl and aralkyl of about 8 to about 30 carbon atoms, and substituted alkyl, alkenyl, aryl, alkaryl, and aralkyl of from about 1 to about 30 carbon atoms wherein the substituents are selected from the group consisting of halogen, carboxyl, and hydroxyl, said composition having a thermal softening point of from about 35° C. to about 100° C.

The tertiary amine and/or ester amine can provide superior odor and/or improved fabric conditioning performance, compared to similar articles which utilize primary amine or ammonium compounds as the sole fabric conditioning active agent and/or hair conditioning active agent. Either $R^4$, $R^5$, $R^6$, $R^7$, $R^8$, and/or $R^9$ chains can contain unsaturation.

In one example, $R^5$ is an aliphatic chain containing from about 12 to about 30 carbon atoms, $R^6$ is an aliphatic chain of from about 1 to about 30 carbon atoms, and $R^4$ is an aliphatic chain of from about 1 to about 30 carbon atoms. In one example, suitable tertiary amines for static control performance are those containing unsaturation; e.g., oleyldimethylamine and/or soft tallowdimethylamine.

Examples of suitable tertiary amines as starting material for the reaction between the amine and carboxylic acid to form the tertiary amine salts are: lauryldimethylamine, myristyldimethyl-amine, stearyldimethylamine, tallowdimethylamine, coconutdimethylamine, dilaurylmethylamine, distearylmethylamine, ditallowmethylamine, oleyldimethylamine, dioleylmethylamine, lauryldi(3-hydroxypropyl)amine, stearyldi(2-hydroxyethyl)amine, trilaurylamine, laurylethylmethylamine, and

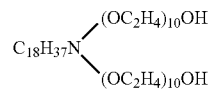

Non-limiting examples of suitable fatty acids are those wherein $R^7$ is a long chain, unsubstituted alkyl or alkenyl group of from about 8 to about 30 carbon atoms and/or from about 11 to about 17 carbon atoms.

Examples of specific carboxylic acids as a starting material are: formic acid, acetic acid, lauric acid, myristic acid, palmitic acid, stearic acid, oleic acid, oxalic acid, adipic acid, 12-hydroxy stearic acid, benzoic acid, 4-hydroxy benzoic acid, 3-chloro benzoic acid, 4-nitro benzoic acid, 4-ethyl benzoic acid, 4-(2-chloroethyl)benzoic acid, phenylacetic acid, (4-chlorophenyl)acetic acid, (4-hydroxyphenyl) acetic acid, and phthalic acid.

Non-limiting examples of suitable carboxylic acids are stearic, oleic, lauric, myristic, palmitic, and mixtures thereof.

The amine salt can be formed by a simple addition reaction, well known in the art and disclosed in U.S. Pat. No. 4,237,155, Kardouche, issued Dec. 2, 1980, which is incorporated herein by reference. Excessive levels of free amines may result in odor problems, and generally free amines provide poorer softening performance than the amine salts.

Non-limiting examples of amine salts for use herein are those wherein the amine moiety is a $C_8$-$C_{30}$ alkyl or alkenyl dimethyl amine and/or a di-$C_8$-$C_{30}$ alkyl or alkenyl methyl amine, and the acid moiety is a $C_8$-$C_{30}$ alkyl and/or alkenyl monocarboxylic acid. The amine and the acid, respectively, used to form the amine salt will often be of mixed chain lengths rather than single chain lengths, since these materials are normally derived from natural fats and oils, or synthetic processed which produce a mixture of chain lengths. Also, it is often desirable to utilize mixtures of different chain lengths in order to modify the physical or performance characteristics of the softening composition.

Specific examples of amine salts for use in the present invention are oleyldimethylamine stearate, stearyldimethylamine stearate, stearyldimethylamine myristate, stearyldimethylamine oleate, stearyldimethylamine palmitate, distearylmethylamine palmitate, distearylmethylamine laurate, and mixtures thereof. In one example, a mixture of amine salts is oleyldimethylamine stearate and distearylmethylamine myristate, in a ratio of 1:10 to 10:1 and/or about 1:1.

Sulfonic Acid Fatty Amine Salts

Other fatty amine salts can be used in the present invention. These salts are similar to those previously described but replacing the carboxylic acid with a sulfonic acid derivative. The amine salt can be formed by a simple addition reaction, well known in the art and disclosed in U.S. Pat. No. 4,861,502, Caswell issued Aug. 29, 1989, which is incorporated herein by reference. Such sulfonic acid derivates include but not limited to methylsulfonic acid, benzenesulfonic acid, toluensulfonic acid, cumenesulfonic and mixtures thereof.

Non-limiting examples of suitable active agents of the present invention include active agents selected from the group consisting of antimicrobial agents (e.g., bacteriocides, fungicides), malodor-absorbing material, and combinations thereof. For example, antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Further non-limiting examples of suitable active agents for use in the 3D articles of the present invention include active agents selected from the group consisting of: astringent metallic salts, like inorganic and organic salts of aluminum, zirconium and zinc, as well as mixtures thereof. For example, the active agent may include zirconium-containing salts or materials, such as zirconyl oxyhalides, zirconyl hydroxyhalides, and mixtures thereof and/or aluminum-containing salts such as, for example, aluminum halides, aluminum chlorohydrate, aluminum hydroxyhalides, and mixtures thereof.

1. Aluminum Salts

Aluminum salts useful herein can include those that conform to the formula:

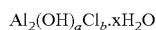

$Al_2(OH)_aCl_b \cdot xH_2O$ wherein a is from about 2 to about 5; the sum of a and b is about 6; x is from about 1 to about 6; where a, b, and x can have non-integer values. For example, aluminum chlorohydroxides referred to as "5/6 basic chlorohydroxide," wherein a is about 5 and "2/3 basic chlorohydroxide", wherein a=4 can be used.

A general description of these aluminum salts can be found in Antiperspirants and Deodorants, Cosmetic Science and Technology Series Vol. 20, 2nd edition, edited by Karl Laden. Mixtures of aluminum salts are described in British Patent Specification 1,347,950, filed in the name of Shin et al. and published Feb. 24, 1974.

2. Zirconium Salts

Zirconium salts useful herein can include those which conform to the formula:

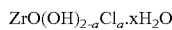

$ZrO(OH)_{2-a}Cl_a \cdot xH_2O$ wherein a is from about 1.5 to about 1.87; x is from about 1 to about 7; and wherein a and x can both have non-integer values. These zirconium salts are described in Belgian Patent 825,146, issued to Schmitz on Aug. 4, 1975. Useful to the present invention are zirconium salt complexes that additionally contain aluminum and glycine, commonly known as "ZAG complexes". These complexes can contain aluminum chlorohydroxide and zirconyl hydroxy chloride conforming to the above-described formulas. Examples of two such complexes include aluminum zirconium trichlorohydrex and aluminum zirconium tetrachlorohydrex.

The antiperspirant active can comprise, for example, aluminum zirconium tetrachlorohydrex glycine; aluminum zirconium tetrachlorohydrate, aluminum zirconium pentachlorohydrate, aluminum zirconium pentachlorohydrex glycine, aluminum zirconium trichlorohydrex glycine, aluminum zirconium trichlorohydrate, aluminum zirconium octachlorohydrate, aluminum zirconium octachlorohydrex glycine, aluminum chlorohydrate, aluminum chlorohydrex polyethylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol or a combination thereof.

Nonionic Fabric Conditioning Active Agents and/or Hair Conditioning Active Agents Non-limiting examples of suitable nonionic fabric conditioning active agents and/or nonionic hair conditioning active agents for use in the fibrous elements and/or films and/or articles of the present invention have an HLB of from about 2 to about 9, and more typically from about 3 to about 7. In general, the materials selected should be relatively crystalline and higher melting, (e.g., >25° C.).

The level of optional nonionic fabric conditioning active agents and/or optional nonionic hair conditioning active agents in the article is typically from about 0.1% to about 50% and/or from about 5% to about 30%.

Non-limiting examples of suitable nonionic fabric conditioning active agents and/or nonionic hair conditioning active agents are fatty acid partial esters of polyhydric alcohols, or anhydrides thereof, wherein the alcohol or anhydride contains from about 2 to about 18 and/or from about 2 to about 8 carbon atoms, and each fatty acid moiety contains from about 8 to about 30 and/or from about 12 to about 20 carbon atoms. Typically, such nonionic fabric conditioning active agents and/or hair conditioning active agents contain from about one to about 3 and/or about 2 fatty acid groups per molecule.

The polyhydric alcohol portion of the ester can be ethylene glycol, glycerol, poly (e.g., di-, tri-, tetra, penta-, and/or hexa-) glycerol, xylitol, sucrose, erythritol, pentaerythritol, sorbitol or sorbitan.

The fatty acid portion of the ester is normally derived from fatty acids having from about 8 to about 30 and/or from about 12 to about 22 carbon atoms. Typical examples of said fatty acids being lauric acid, myristic acid, palmitic acid, stearic acid, oleic acid, and behenic acid.

Non-limiting example of suitable nonionic fabric conditioning active agents and/or hair conditioning active agents for use in the present invention are $C_{10}$-$C_{26}$ acyl sorbitan esters and polyglycerol monostearate. Sorbitan esters are esterified dehydration products of sorbitol. The sorbitan ester may comprise a member selected from the group consisting of $C_{10}$-$C_{26}$ acyl sorbitan monoesters and/or $C_{10}$-$C_{26}$ acyl sorbitan diesters and/or ethoxylates of said esters wherein one or more of the unesterified hydroxyl groups in said esters contains from about 1 to about 6 oxyethyl-ene units, and mixtures thereof. For the purpose of the present invention, sorbitan esters containing unsaturation (e.g., sorbitan monooleate) can be utilized.

Sorbitol, which is typically prepared by the catalytic hydrogenation of glucose, can be dehydrated in well known fashion to form mixtures of 1,4- and 1,5-sorbitol anhydrides and small amounts of isosorbides. (See U.S. Pat. No. 2,322,821, Brown, issued Jun. 29, 1943, incorporated herein by reference.)

The foregoing types of complex mixtures of anhydrides of sorbitol are collectively referred to herein as "sorbitan." It will be recognized that this "sorbitan" mixture will also contain some free, uncyclized sorbitol.

In one example, the sorbitan fabric conditioning active agents and/or hair conditioning active agents of the type employed herein can be prepared by esterifying the "sorbitan" mixture with a fatty acyl group in standard fashion, e.g., by reaction with a fatty acid halide, fatty acid ester, and/or fatty acid. The esterification reaction can occur at any of the available hydroxyl groups, and various mono-, di-, etc., esters can be prepared. In fact, mixtures of mono-, di-, tri-, etc., esters almost always result from such reactions, and the stoichiometric ratios of the reactants can be simply adjusted to favor the desired reaction product.

For commercial production of the sorbitan ester materials, etherification and esterification are generally accomplished in the same processing step by reacting sorbitol directly with fatty acids. Such a method of sorbitan ester preparation is described more fully in MacDonald, "Emulsifiers: Processing and Quality Control", *Journal of the American Oil Chemists' Society*, Vol. 45, October 1968. Details, including formula, of the examples of sorbitan esters can be found in U.S. Pat. No. 4,128,484, incorporated hereinbefore by reference.

Certain derivatives of the sorbitan esters herein, especially the "lower" ethoxylates thereof (i.e., mono-, di-, and tri-esters wherein one or more of the unesterified —OH groups contain one to about twenty oxyethylene moieties (Tweens®) are also useful in the articles of the present invention. Therefore, the term "sorbitan ester" is intended to include such derivatives.

For the purposes of the present invention, in one example, a significant amount of di- and tri-sorbitan esters are present in the ester mixture. In another example, an ester mixture may have from about 20-50% mono-ester, about 25-50% di-ester and about 10-35% of tri- and tetra-esters. Material which is sold commercially as sorbitan mono-ester (e.g., monostearate) typically contains significant amounts of di- and tri-esters. A typical analysis of commercial sorbitan monostearate indicates that it comprises about 27% mono-, about 32% di- and about 30% tri- and tetra-esters. Mixtures of sorbitan stearate and sorbitan palmitate having stearate/palmitate weight ratios varying between 10:1 and 1:10, and 1,5-sorbitan esters are also useful. In addition, both the 1,4- and 1,5-sorbitan esters are useful herein.

Other useful alkyl sorbitan esters for use as fabric conditioning active agents and/or hair conditioning active agents herein include sorbitan monolaurate, sorbitan monomyristate, sorbitan monopalmitate, sorbitan monobehenate, sorbitan monooleate, sorbitan dilaurate, sorbitan dimyristate, sorbitan dipalmitate, sorbitan distearate, sorbitan dibehenate, sorbitan dioleate, and mixtures thereof, and mixed tallowalkyl sorbitan mono- and di-esters. Such mixtures are readily prepared by reacting the foregoing hydroxy-substituted sorbitans, particularly the 1,4- and 1,5-sorbitans, with the corresponding acid, ester, or acid chloride in a simple esterification reaction. It is to be recognized, of course, that commercial materials prepared in this manner will comprise mixtures usually containing minor proportions of uncyclized sorbitol, fatty acids, polymers, isosorbide structures, and the like. In the present invention, it is desirable to keep such impurities present at as low a level as practical.

The sorbitan esters employed herein may contain up to about 15% by weight of esters of the $C_{20}$-$C_{26}$, and higher, fatty acids, as well as minor amounts of $C_8$, and lower, fatty esters.

Glycerol and polyglycerol esters, especially glycerol, diglycerol, triglycerol, and polyglycerol mono- and/or di-esters, in one example mono- (e.g., polyglycerol monostearate with a trade name of Radiasurf 7248). Glycerol esters can be prepared from naturally occurring triglycerides by normal extraction, purification and/or interesterification processes or by esterification processes of the type set forth hereinbefore for sorbitan esters. Partial esters of glycerin can also be ethoxylated to form usable derivatives that are included within the term "glycerol esters."

Useful glycerol and polyglycerol esters include monoesters with stearic, oleic, palmitic, lauric, isostearic, myristic, and/or behenic acids and the diesters of stearic, oleic, palmitic, lauric, isostearic, behenic, and/or myristic acids. It is understood that the typical mono-ester contains some di- and tri-ester, etc.

The "glycerol esters" also include the polyglycerol, e.g., diglycerol through octaglycerol esters. The polyglycerol polyols are formed by condensing glycerin or epichlorohydrin together to link the glycerol moieties via ether linkages. The mono- and/or diesters of the polyglycerol polyols may be used, the fatty acyl groups typically being those described hereinbefore for the sorbitan and glycerol esters.

Fatty Fabric Conditioning Active Agents and/or Hair Conditioning Active Agents

The fibrous elements and/or films and/or articles of the present invention further comprise one or more fatty fabric conditioning active agents and/or fatty hair conditioning active agents, for example one or more high melting point fatty compounds. The high melting point fatty compound can be included in the composition at a level of from about 10 wt % to about 85 wt % and/or from 20 wt % to 70 wt % and/or from about 50 wt % to about 70 wt % and/or from about 10 wt % to about 20 wt % of the fibrous element and/or film and/or article. In one example, the fatty fabric conditioning active agent and/or fatty hair conditioning active agent is selected from the group consisting of: fatty amphiphiles, fatty alcohols, fatty acids, fatty amides, fatty esters and mixtures thereof.

In one example, the fatty fabric conditioning active agents and/or fatty hair conditioning active agents have a melting point of 25° C. or higher and/or 40° C. or higher and/or 45° C. or higher and/or 50° C. or higher and/or to about 90° C. and/or to about 80° C. and/or to about 70° C. and/or to about 65° C. and are considered as high melting point fatty fabric conditioning active agents and/or high melting point fatty hair conditioning active agents. The fatty fabric conditioning active agent and/or fatty hair conditioning active agent may be used as a single compound or as a blend or mixture of at least two fatty fabric conditioning active agents and/or a mixture of at least two fatty hair conditioning active agents. When used as such blend or mixture, the above melting point means the melting point of the blend or mixture.

The fatty fabric conditioning active agents and/or fatty hair conditioning active agents useful herein may be selected from the group consisting of fatty alcohols, fatty acids, fatty alcohol derivatives, fatty acid derivatives, and mixtures thereof. It is understood by the artisan that the fatty fabric conditioning active agents and/or fatty hair conditioning active agents disclosed herein may in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain fatty fabric conditioning active agents and/or fatty hair conditioning active agents having certain required carbon atoms may have a melting point of less than the above. Such fatty fabric conditioning active agents and/or fatty hair conditioning active agents of low melting point (a melting point less than 25° C. and/or less than 20° C.) are not intended to be included in this section. Non-limiting examples of the high melting point fatty fabric conditioning active agents and/or high melting point fatty hair conditioning active agents are found in International Cosmetic Ingredient Dictionary, Fifth Edition, 1993, and CTFA Cosmetic Ingredient Handbook, Second Edition, 1992.

Fatty Acids

The fabric conditioning active agents and/or hair conditioning active agents in the articles of the present invention may further comprise one or more fatty acids. Typically, the fatty acid is present to improve the processability of the composition, and is admixed with any material, or materials, that are difficult to process, especially as a result of having a high viscosity. The fatty acid provides improved viscosity and/or processability, without harming softening or antistatic performance of the article.

Non-limiting examples of suitable fatty acids are those containing a long chain, unsubstituted alkenyl group of from about 8 to about 30 carbon atoms and/or from about 11 to about 18 carbon atoms. Examples of specific carboxylic acids are: oleic acid, linoleic acid, and mixtures thereof. Although unsaturated fatty acids are desirable, the unsaturated fatty acids can also be used in combination with saturated fatty acids like stearic, palmitic, and/or lauric acids. Non-limiting examples of suitable carboxylic acids are oleic, linoleic, tallow fatty acids, and mixtures thereof.

In one example, the fatty acid is added to the quaternization reaction mixture used to form the biodegradable quaternary ammonium compounds of Formulas II, III, and/or IV as described hereinbefore to lower the viscosity of the reaction mixture to less than about 1500 cps and/or less than about 1000 cps and/or less than about 800 cps. The solvent level of added fatty acid may be from about 5% to about 30% and/or from about 10% to about 25% and/or from about 10% to about 20%. The unsaturated fatty acid can be added before the start of the quaternization reaction and/or may be added during the quaternization reaction when it is needed to reduce the viscosity which increases with increased level of quaternization. In one example, the addition occurs when at least about 60% of the product is quaternized. This allows for a low viscosity for processing while minimizing side reactions that can occur when the quaternizing agent reacts with the fatty acid. The quaternization reactions are well known and include, e.g., with respect to Formula IA and/or IB compounds, those processes described in U.S. Pat. No. 3,915,867, Kang et al., issued Oct. 28, 1975; U.S. Pat. No. 4,830,771, Ruback et al., issued May 16, 1989; and U.S. Pat. No. 5,296,622, Uphues et al., issued Mar. 22, 1994, all of said patents being incorporated herein by reference. The resulting quaternized biodegradable fabric conditioning active agents can be used without removal of the unsaturated fatty acid, and, in fact, are more useful since the mixture is more fluid and more easily handled.

Another example of a type of fabric conditioning active agents and/or hair conditioning active agents is described in detail in U.S. Pat. No. 4,661,269, Toan Trinh, Errol H. Wahl, Donald M. Swartley and Ronald L. Hemingway, issued Apr. 28, 1987, said patent being incorporated herein by reference Fatty Alcohols Non-limiting examples of suitable fatty alcohols useful as fatty fabric conditioning active agents and/or fatty hair conditioning active agents are those fatty alcohols having from about 14 to about 30 carbon atoms and/or from about 16 to about 22 carbon atoms. These fatty alcohols are saturated and can be straight or branched chain alcohols.

Suitable fatty alcohols include, but are not limited to, cetyl alcohol (having a melting point of about 56° C.), stearyl alcohol (having a melting point of about 58-59° C.), behenyl alcohol (having a melting point of about 71° C.), and mixtures thereof. These fatty alcohols are known to have the above referenced melting points, however, they often have lower melting points when supplied, since such supplied products are often mixtures of fatty alcohols having alkyl chain length distributions in which the main alkyl chain is cetyl, stearyl or behenyl group. Generally, in the mixture, the weight ratio of cetyl alcohol to stearyl alcohol can be from about 1:9 to 9:1 and/or from about 1:4 to about 4:1 and/or from about 1:2.3 to about 1.5:1.

Dispersing Agents

In one example, the fabric conditioning active agents and/or hair conditioning active agents may comprise a dispersing agent. The dispersing agent, when present, greatly increases the wetting, hydration, and dispersion of the fabric conditioning active agents and/or hair conditioning active agents. The dispersing agent can be included at a level of from about 1 wt % to about 30 wt % of the composition, alternatively from about 5 wt % to about 15 wt %, and alternatively from about 5 wt % to about 10 wt %. A surfactant from the nonionic class of alkyl glucamides can improve the wetting and hydration when added to the solid conditioner formula. The alkyl glucamide surfactant contains a hydrophobic tail of about 8-18 carbons and a nonionic head group of glucamide. For glucamide, the presence of the amide and hydroxyl groups may provide sufficient polarity that balances the hydrophobic carbon tail in such a way to permit the surfactant's solubility in the conditioner oils and also imparts a rapid dispersion of the conditioner ingredients upon exposure to water. Other similar dispersing agents include, but are not limited to, reverse alkyl glucamides, cocoamidopropyl betaines, alkyl glucoside, Triethanol amine, cocamide MEAs and mixtures thereof.

Cationic Surfactants

The fabric conditioning active agent and/or hair conditioning active agent of the present invention may comprise a cationic surfactant. When present, the cationic surfactant may be present at a level of from about 1 wt % to about 60 wt %, alternatively from about 10 wt % to about 50 wt %, alternatively from about 20 wt % to about 40 wt % of the article.

Cationic surfactants useful herein can be one cationic surfactant or a mixture of two or more cationic surfactants. The cationic surfactant can be selected from the group consisting of, but not limited to: a mono-long alkyl quaternized ammonium salt; a combination of a mono-long alkyl quaternized ammonium salt and a di-long alkyl quaternized ammonium salt; a mono-long alkyl amine; a combination of a mono-long alkyl amine and a di-long alkyl quaternized ammonium salt; and a combination of a mono-long alkyl amine and a mono-long alkyl quaternized ammonium salt, a tertiary amine and combinations thereof.

Mono-Long Alkyl Amines

Mono-long alkyl amine useful herein are those having one long alkyl chain of from 12 to 30 carbon atoms, alternatively from 16 to 24 carbon atoms, alternatively from 18 to 22 alkyl group. Mono-long alkyl amines useful herein also include mono-long alkyl amidoamines. Primary, secondary, and tertiary fatty amines are useful.

Suitable for use in the articles of the present invention are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines can be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; alternatively l-glutamic acid, lactic acid, citric acid, at a molar ratio of the amine to the acid of from about 1:0.3 to about 1:2, alternatively from about 1:0.4 to about 1:1.

Mono-Long Alkyl Quaternized Ammonium Salts

The mono-long alkyl quaternized ammonium salts useful herein are those having one long alkyl chain which has from 12 to 30 carbon atoms, alternatively from 16 to 24 carbon atoms, alternatively a C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the following formula (V):

(V)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. One of $R^{75}$, $R^{76}$, $R^{77}$ and $R^{78}$ can be selected from an alkyl group of from 12 to 30 carbon atoms, alternatively from 16 to 24 carbon atoms, alternatively from 18 to 22 carbon atoms, alternatively 22 carbon atoms; the remainder of $R^{75}$, $R^{76}$, $R^{77}$ and $R^{78}$ can be independently selected from $CH_3$, $C_2H_5$, $C_2H_4OH$, and mixtures thereof; and X can be selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Di-Long Alkyl Quaternized Ammonium Salts

When used, di-long alkyl quaternized ammonium salts can be combined with a mono-long alkyl quaternized ammonium salt and/or mono-long alkyl amine salt, at the weight ratio of from 1:1 to 1:5, alternatively from 1:1.2 to 1:5, alternatively from 1:1.5 to 1:4, in view of stability in rheology and conditioning benefits.

Di-long alkyl quaternized ammonium salts useful herein are those having two long alkyl chains of from 12 to 30 carbon atoms, alternatively from 16 to 24 carbon atoms, alternatively from 18 to 22 carbon atoms. Such di-long alkyl quaternized ammonium salts useful herein are those having the formula (VI):

(VI)

wherein two of $R^{71}$, $R^{72}$, $R^{73}$ and $R^{74}$ are selected from an aliphatic group of from 12 to 30 carbon atoms, alternatively from 16 to 24 carbon atoms, alternatively from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, alternatively from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Two of $R^{71}$, $R^{72}$, $R^{73}$ and $R^{74}$ can be selected from an alkyl group of from 12 to 30 carbon atoms, alternatively from 16 to 24 carbon atoms, alternatively from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Suitable di-long alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Auxiliary Ingredients

In addition to the one or more active agents, the 3D articles of the present invention may further comprises one or more auxiliary ingredients, for example one or more structurants and/or one or more fillers. The one or more auxiliary ingredients, for example one or more structurants and/or one or more fillers, when present, may be dispersed throughout, for example homogeneously dispersed throughout, the one or more active agents within the 3D article-forming composition and/or 3D article. When present, the one or more auxiliary ingredients may be present in the 3D article-forming composition and/or 3D article at a total level of less than 20% or less and/or less than 15% and/or less than 10% and/or less than 5% and/or less than 4% and/or less than 3% and/or less than 2% and/or less than 1% and/or about 0% by weight on a dry 3D article-forming composition and/or dry 3D article basis.

Structurants

In one example, the 3D article-forming material is a structurant. A "structurant" as used herein means a material, for example a polymer, that may improve the 3D article 3D printing and/or extruding of the active agents (melted and/or flowable active agents), such as fatty alcohols, fatty quaternary ammonium compounds, fatty acids, etc. The structurant increases the shear viscosity (flow rheology) and extensional viscosity (extensional rheology) of the melted active agents. In one example, the structurant can be included at a level of from about 1 wt % to about 50 wt % and/or from about 1 wt % to about 30 wt % and/or from about 1 wt % to about 10 wt % and/or from about 2 wt % to about 6 wt % and/or from about 3 wt % to about 5 wt % of the 3D article-forming composition. In one example, the structurant exhibits a weight average molecular weight of from about 10,000 to about 6,000,000 g/mol. The weight average molecular weight is computed by summing the average molecular weights of each polymer raw material multiplied by their respective relative weight percentages by weight of the total weight of polymers present within the 3D article. However, a balance is often struck between concentration and molecular weight, such that when a lower molecular weight species is used, it requires a higher level to result in optimal 3D printing and/or extruding. Likewise, when a higher molecular species is used, lower levels can be used to achieve optimal 3D printing and/or extruding. For example, a structurant having a molecular weight of from about 3,000,000 g/mol to about 5,000,000 g/mol may be included at a level of from about 3 wt % to about 6 wt % whereas a structurant having a molecular weight of from about 50,000 g/mol to about 100,000 g/mol may be included at a level of from about 30 wt % to about 50 wt %. In one example, the structurant is soluble in an oily mixture to enable viscosity build for 3D article 3D printing and/or extruding. In addition, the structurant may also be soluble in water to promote removal and to prevent buildup.

Non-limiting examples of suitable structurants are selected from the group consisting of: polymeric structurants, inorganic structurants, and mixtures thereof. In one example, the auxiliary ingredient, for example structurant, comprises a polymeric structurant selected from the group consisting of: polyvinylpyrrolidone, copolymers of vinylpyrrolidone, polydimethylacrylamide, copolymers of dimethylacrylamide, and mixtures thereof. In one example, the structurant comprises polyvinylpyrrolidone. In one example, the structurant comprises polydimethylacrylamide. In one example, the structurant comprises an inorganic structurant selected from the group consisting of clays, silica, and mixtures thereof.

Other non-limiting examples of suitable structurants include gelling agents for example gelling agents selected from the group consisting of: fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof. In one example, suitable gelling agents include fatty acid gellants such as fatty acid and hydroxyl or alpha hydroxyl fatty acids, having from about 10 to about 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents are 12-hydroxystearic acid, esters of 12-hydroxystearic acid, amides of 12-hydroxystearic acid and combinations thereof.

Other suitable gelling agents include amide gellants such as di-substituted or branched monoamide gellants, monsubstituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. Pat. No. 5,840,287, filed Dec. 20, 1996.

Still other examples of suitable gelling agents include fatty alcohols having at least about 8 carbon atoms, at least about 12 carbon atoms but no more than about 40 carbon atoms, no more than about 30 carbon atoms, or no more than about 18 carbon atoms. For example, fatty alcohols include but are not limited to cetyl alcohol, myristyl alcohol, stearyl alcohol and combinations thereof.

The one or more structurants, when present, may be dispersed throughout, for example homogeneously, the one or more active agents within the 3D article-forming composition and/or 3D article. When present, the one or more structurants may be present in the 3D article-forming composition and/or 3D article at a total level of less than 20% or less and/or less than 15% and/or less than 10% and/or less than 5% and/or less than 4% and/or less than 3% and/or less than 2% and/or less than 1% and/or about 0% by weight on a dry 3D article-forming composition and/or dry 3D article basis.

Suitable structurants include, but are not limited to, polyvinylpyrrolidone, polydimethylacrylamides, and combinations thereof. These polymers are oil (fatty alcohol, fatty acid, fatty quaternary ammonium compounds) soluble, water soluble, and capable of being produced at high molecular weights. For example, suitable polymers for use are PVP K120 from Ashland Inc., having a molecular weight of about 3,500,000 g/mol, which is soluble in oil and water and enables fibrous elements to be formed and collected onto a belt. Additional suitable polymers include copolymers of polyvinylpyrrolidone, such as Ganex® or PVP/VA (weight average molecular weight of about 50,000 g/mol) copolymers from Ashland Inc., which also function as suitable structurants but require a higher level to be effective due to their lower molecular weights. In addition, copolymers of polydimethylacrylamide also function as suitable structurants. Hydroxyl propyl cellulose can also function as a suitable structurant.

Non-limiting examples of structurants suitable for the present invention include polymeric structurants, inorganic structurants, and mixtures thereof. In one example, the structurant comprises a polymeric structurant selected from the group consisting of: polylactams such as polyvinylpyrrolidone and copolymers of vinylpyrrolidone, polydimethylacrylamide, copolymers of dimethylacrylamide, and mixtures thereof. In one example, the structurant comprises polyvinylpyrrolidone. In another example, the structurant comprises polydimethylacrylamide. In still another example, the structure comprises polyvinylpyrrolidone and polydimethylacrylamide. In one example, the structurant comprises inorganic structurants selected from the group consisting of clays, silica, and mixtures thereof.

As used herein, "vinyl pyrrolidone copolymer" (and "copolymer" when used in reference thereto) refers to a polymeric structurant of the following structure:

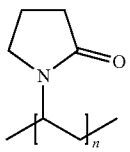

wherein n is an integer such that the polymeric structurant has the degree of polymerization such that it possesses characteristics described herein. For purposes of clarity, the use of the term "copolymer" is intended to convey that the vinyl pyrrolidone monomer can be copolymerized with other non-limiting monomers such as vinyl acetate, alkylated vinyl pyrrolidone, vinyl caprolactam, acrylic acid, methacrylate, acrylamide, methacrylamide, dimethacrylamide, alkylaminomethacrylate, and alkylaminomethacrylamide monomers.

Fillers

In one example, the 3D article-forming material is an auxiliary ingredient comprising a filler. A "filler" as used herein means a solid additive, for example a particle, such as a powder, granule, encapsulate, microcapsule, and/or prill, that may improve the 3D article 3D printing and/or extruding of the melted active agents, such as fatty alcohols, fatty quaternary ammonium compounds, fatty acids, etc. The filler increases the shear viscosity (flow rheology) of the melted active agents. In one example, the filler exhibits a median particle size of 2000 μm or less as measured according to the Median Particle Size Test Method described herein. In another example, the filler exhibits a median particle size of from about 1 μm to about 2000 μm and/or from about 1 μm to about 1600 μm and/or from about 1 μm to about 800 μm and/or from about 5 μm to about 500 μm and/or from about 10 μm to about 300 μm and/or from about 10 μm to about 100 μm and/or from about 10 μm to about 50 μm and/or from about 10 μm to about 30 μm as measured according to the Median Particle Size Test Method described herein. The shape of the filler can be in the form of spheres, rods, plates, tubes, squares, rectangles, discs, stars, fibers or have regular or irregular random forms. In one example, the median filler particle size is smaller than the radius of the extrusion or 3D printing nozzle. In another example, the median filler particle size is less than 0.5 times the extrusion or 3D printing nozzle radius. In another example, the median filler particle size is less than 0.1 times the extrusion or 3D printing nozzle radius.

Fillers may be organic, inorganic or of mixed inorganic/organic nature that are solid at processing temperatures used to make the 3D article. Non-limiting examples of suitable fillers are selected from the group consisting of: starches, gums, polysaccharides, proteins, amino acids, water soluble polymers, water degradable polymers, water-insoluble polymers, sugars, sugar alcohols, organic salts, inorganic particles, organic salts and mixtures thereof.

Starches may be sourced from plant materials including: corn, wheat, potato, rice, cassava and tapioca. Starches may be unmodified, modified, or partially degraded. Modified starch may include cationic starch, hydroxyehtyl starch, carboxymethylated starch, and polylactic acid graft-starch and polycaprylactone graft starch. Degraded starches may include dextrin and maltodextrin preferably with a dextrose equivalent of 30 or lower.

Gums can be extracted from natural sources, modified from natural sources or fermented. Suitable natural sources from gums include trees, plants, animals and seeds. Examples of natural gums include gum acacia, gum tragacanth, gum karaya, gum ghatti, nanocrylstalline cellulose, pectin, carrageenan, agar, furcellaran, konjac gum, gelatin, guar gum, locast bean gum, tara gum, cassia gum, mesquite gum, tamarind seed gum, quince seed gum, flaxseed gum, phyllium seed gum, oat gum, and microfibrillated cellulose. Gums may also be modified to create alkali cellulose, salts of carboxymethylcellulose, methylcellulose, hydroxypropyl methylcellulose, hydroxypropyl cellulose and hydroxyethyl cellulose. Examples of fermented gums are xanthan gum, dextran and pullulan.

Suitable water-soluble polymers may be synthesized using vinyl addition reaction or ring opening synthesis. Examples of vinyl addition polymers are polyvinyl alcohol, poly(acrylic acid), poly(methacrylic acid), Poly(2-dimethylamino ethyl methacrylate) methyl chloride quaternary salt, Poly(2-dimethylamino ethylacrylate) methyl chloride quaternary salt, poly(allylamine), polyacrylamide, polymethacrylamide, poly [n-(2-hydroxypropyl) methacrylamide], Poly((3-acrylamidopropyl)trimethylammonium chloride), poly(n-(2-aminoethyl) methacrylamide hydrochloride quantized salt), poly(N-isopropylacrylamide), poly(diallyl dimethyl ammonium chloride), poly(styrenesulfonic acid), and poly(vinyl phosphoric acid). Examples of ring opening synthesized polymers include poly(2-oxazoline), poly(2-ethyl-2-oxazoline), polyethyleneimine, poly(maleic anhydride), and polyaspartic acid. Water soluble copolymers such as poly(vinyl alcohol)-co-poly(ethylene glycol) available as Kollicoat® from BASF.

Water degradable polymers typically contain an ester bond in their backbone leading to hydrolysis in water. Examples of water degradable polymers are polylactic acid, polyglycolic acid, polybutylene succinate, polycaprolactone, polybutyrate, and poly(glycolic acid-co-lactic acid).

Examples of water-insoluble polymers include nylon, polystyrene, polyurethane, polyvinyl chloride, polytetrafluoroethylene, latex and polyethylene. Latex may be natural rubber or synthetic. Commonly available synthetic latexes include nitrile rubber, polychloroprene, butyl rubber, fluorocarbon rubber, polyurethane, styrene-butadiene rubber and blends thereof. Polyethylene particles are available under the tradename VELUSTROL from HOECHST Aktiengesellschaft of Frankfurt am Main, Germany.

Examples of sugars and sugar alcohols include glucose, fructose, galactose, sucrose, maltose, lactose and trehalose. Examples of sugar alcohols include erythritol, threitol, arabitol, ribitol, xylitol, mannitol, sorbitol, galactitol, iditol, volemitol, fucitol, inositol, maltitol and lactitol.

Examples of inorganic particles include silica, fumed silica, precipitated silica, talcum powder, graphite, aluminum oxide, iron oxide, antimony trioxide, copper, bentonite clay, laponite clay, aluminium silicate clay, calcium carbonate, sodium chloride, magnesium chloride, calcium chloride, tetramethyl ammonium chloride, alumina, titanium dioxide, chalk, titanium hydroxide, gypsum powder and sodium sulfate.

Examples of organic salts include choline chloride, betaine, sorbic acid, and uric acid.

The fillers may be water-soluble or water-insoluble. In one example, one group of particles may be water-soluble and a different group of particles may be water-insoluble. The fillers, water-soluble or water-insoluble, may themselves deliver a benefit to the consumer. In another example, the fillers, water-soluble or water-insoluble, may comprise one or more active agents (in other words, the particles may comprise active agent-containing particles). In still another example, the fillers may consist essentially of and/or consist of one or more active agents (in other words, the particles, water-soluble and/or water-insoluble, may comprise 100% or greater than about 100% by weight on a dry particle basis of one or more active agents). In still another example, the fillers may comprise water-soluble particles. In yet another example, the fillers may comprise water-soluble, active agent-containing particles. In one other example, the water-insoluble fillers comprise zeolites, porous zeolites, perfume-loaded zeolites, active loaded zeolites, silicas, perfume-loaded silicas, active loaded silicas, perfume microcapsules, clays, and mixtures thereof.

Optional Ingredients

In addition to the one or more fabric conditioning active agents and/or hair conditioning active agents described above, the 3D articles of the present invention may further comprise one or more optional ingredients. When present, the one or more optional ingredients may be present in and/or on the 3D article at a level of from about 0.01% to about 30% and/or from about 0.1% to about 20% and/or from about 0.1% to about 5% by weight of the 3D article. Non-limiting examples of such optional ingredient include soil release agents, such as soil release polymers, for example soil release polymer that comprise copolymeric blocks of terephthalate and polyethylene oxide or polypropylene oxide, and cationic soil release agents, anti-oxidants, colorants, preservatives, optical brighteners, opacifiers, stabilizers such as guar gum and polyethylene glycol, anti-shrinkage agents, anti-wrinkle agents, soil release agents, fabric crisping agents, reductive agents, spotting agents, germicides, fungicides, anti-corrosion agents, antifoam agents, and the like.

In one example, the optional ingredients may comprise: polymers, perfumes, pro-perfumes, finishing aids, malodor control and removal agents, odor neutralizers, polymeric dye transfer inhibiting agents, cationic deposition enhancing polymers, builders, heavy metal ion sequestrants, surfactants, suds stabilizing polymers, pH modifiers, buffering agents, alkalinity sources, fabric softeners, antistatic agents, dye fixatives, dye abrasion inhibitors, wrinkle reduction agents, wrinkle resistance agents, wrinkle release agents, silicones, soil release polymers, soil repellency agents, colorants, pigments, buttering agents, aversive agents, anti-redeposition agents, bleach activators, bleach catalysts, bleach boosters, bleaches, photobleaches, enzymes, coenzymes, enzyme stabilizers, crystal growth inhibitors, anti-tarnishing agents, anti-oxidants, metal ion salts, corrosion inhibitors, antiperspirant, zinc pyrithione, plant derivatives, plant extracts, plant tissue extracts, plant seed extracts, plant oils, botanicals, botanical extracts, essential oils, skin sensates, astringents, anti-acne agents, anti-dandruff agents, antifoaming agents, cosmetic astringents, cosmetic biocides, denaturants, drug astringents, external analgesics, film formers or materials, e.g., polymers, for aiding the film-forming properties and substantivity of the composition, skin bleaching and lightening agents, skin-conditioning agents, skin soothing and/or healing agents and derivatives, skin treating agents, sunscreen agents, insect repellants, vitamins, anti-bacterial agents, anti-microbial agents, antifungal agents, sun fade inhibiting agents, UV absorbing agents, antioxidants, scents, perfume delivery systems, hueing dyes, and mixtures thereof.

In one example, the optional ingredient comprises an aversive agent, such as a bitterant material or a pungent material to deter or prevent ingestion of an article incorporating the aversive material, e.g. by a child or animal. The bitterant adds a bitter taste to the article to which it is added. Suitable bitterants include denatonium salts (e.g., denatonium benzoate, denatonium saccharide, denatonium chloride), sucrose octaacetate, quinine, flavonoids (e.g., quercetin, naringen), and quassinoids (e.g., quassin, brucine). The pungent adds a sharp biting taste when ingested and a burning sensation when topically applied to the skin. Suitable pungents include capsaicin, piperine, allyl isothiocyanate, and resinferatoxin. Suitable levels of incorporation vary according to the particular bitterant or pungent material. As understood by the skilled artisan, the aversive component should be incorporated as a level sufficiently high to impart the unpleasant taste or sensation, yet sufficiently low to avoid potential toxicity from the aversive itself. Denatonium benzoate is particularly suitable in this regard, as its bitterness threshold is substantially lower than its toxicity threshold.

Method for Making 3D Article-Forming Composition

The 3D article-forming composition of the present invention may be made by any suitable process so long as the 3D article-forming composition is suitable for making the 3D article of the present invention.

In one example, one or more active agents, for example one or more fabric conditioning active agents and/or hair conditioning active agents, are added (in the absence of free water) to a metal beaker and heated to a temperature sufficient to melt the active agents, for example 80° C. The active agents are melted and optionally agitated until they form a homogeneous fluid.

After melting the active agents, one or more auxiliary ingredients, for example one or more 3D article-forming materials, such as one or more structurants, may be added to the homogeneous fluid of active agents. The auxiliary ingredients, when added, are stirred into the homogeneous fluid of active agents until the auxiliary ingredients are homogeneuously dispersed throughout the homogeneous fluid of active agents and/or are homogeneously dissolved within the homogeneous fluid of active agents. This all occurs while maintaining the homogeneous fluid of active agents at a temperature of at least the melting point of the lowest melting point active agent, for example 80° C.

The 3D article-forming composition may then be used to make the 3D articles of the present invention.

Method for Making 3D Article

The 3D articles of the present invention may be made by any suitable 3D printing process and/or extrusion process.

A non-limiting example of a suitable 3D printing process for making the 3D articles is described below.

In one example, a 3D article of the present invention may be made by the following steps:
 a. subjecting one or more active agents to a temperature sufficient to melt the active agents, such as greater than 70° C. and/or from about 75° C. to about 100° C. and/or from about 80° C. (in the absence of water) to form a 3D article-forming composition;
 b. producing one or more 3D articles from the 3D article-forming composition to form a 3D article according to the present invention.

In one example, the 3D articles of the present invention may be made by any suitable 3D article making process such as extrusion and/or 3D printing, such as additive manufacturing.

In one example, the method for manufacturing a 3D article comprises the steps of:

a) providing a digital description of the object as a set of voxels;

b) sequentially creating an actual set of voxels corresponding to the digital set of voxels; wherein at least one voxel comprises at least 30% by weight of one or more active agents, optionally one or more auxiliary ingredients, for example one or more structurants, and optionally one or more additives. The 3D article made from the manufacturing method may exhibit a Bounding Box Density of less than 0.80 g/cm$^3$ as measured according to the μCT Test Method and/or a Free Melt Flow more than about 20% as measured according to the 3D Free Melt Flow Test Method.

The digital description of the 3D article as a set of voxels may be the result of a digital design process using computer aided design software to create a representation of the object. In one embodiment, the digital description may be result of scanning an object to create a digital representation of the object. The initial scanning of the object may result in a digital file which may be enhanced or otherwise altered using appropriate software. In one embodiment, a set of two dimensional images may be interpolated to yield a three dimensional representation of the object as an array or sequence of voxels. The digital description may be provided as a .stl or other known file format.

The provided digital description may be translated to an actual 3D article by the creation of an actual set of voxels corresponding to the set of voxels in the digital representation. This translation may be accomplished using known additive manufacturing techniques including material extrusion techniques. Exemplary apparatus for the translation include fused deposition modeling (FDM) where each digital voxel is translated to an actual voxel by depositing a single liquid drop of material from a nozzle onto a build platform that freezes, cures or hardens to form the actual voxel. The nozzle and/or build-platform move to allow for at least three dimensions of orthogonal motion relative to one another. Voxels are typically deposited to form a two dimensional layer and then another layer of fluid material is deposited over the preceding layer to form the three dimensional object. The liquid droplet size and the distance between the dispensing nozzle and the proceeding layer control voxel size. Material for extrusion through the nozzle may be in a filament, pellet, powder or liquid form. A plurality of build materials may be used. It is preferred that the build-platform, nozzle and any liquid reservoir is temperature controlled. Forced air may be used to provide additional temperature control. The final object may be post processed using any known methods including sanding, polishing and chemical vapor treatment to improve surface finish.

FDM may incorporate the use of a material reservoir and heating system, where powders or pellets of the target material are heated to a point where the materials may flow through the deposition system nozzle or print head. In one embodiment, the material may be provided as a filament. The filament may be rigid or flexible. Exemplary filament cross-section dimensions range from a few tenths of a millimeter to about 10 millimeters are substantially circular. Filaments may be extruded from a reservoir of material heated beyond the glass transition temperature of the material and subsequently cured after extrusion, as is known in the art. The filament may be extruded through a die. The die may be circular, oval, square, rectangular or another shape. A circular die may be preferred. The length of the filament may be substantially greater than the dimensions of the filament cross-section. The filament may be festooned or coiled, or otherwise collected. Alternatively, the material may be formed into pellets rather than a filament. The created filament or pellets may be supplied as a material for 3D printing.

In one example, each voxel of the set of voxels of the actual article is comprised of substantially the same material as all other voxels of the set. Alternatively, respective portions of the overall set of voxels may be comprised of differing materials.

Figure 4:
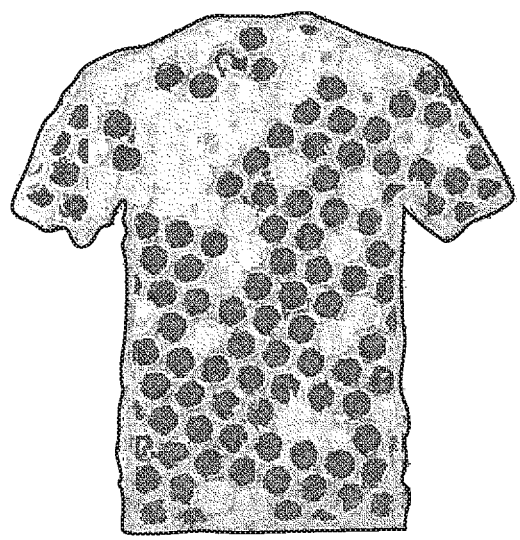
FIG. 4 is an image of another example of a 3D article according to the present invention, which in this case is a 3D printed 3D article.
Figure 5:
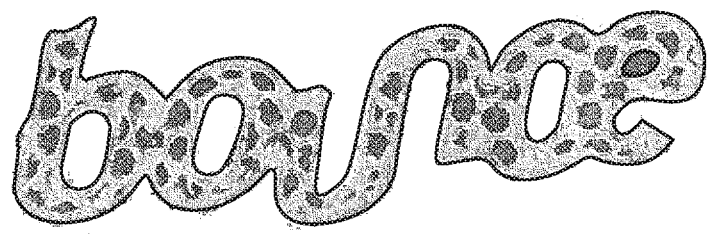
FIG. 5 is an image of another example of a 3D article according to the present invention, which in this case is a 3D printed 3D article.

In one example, the shape of the 3D printed article denotes the product use or Brand. For example, depicting the shape of a laundry item like a shirt (for example as shown in FIG. 4), sock or pants or spelling out a brand name (for example as shown in FIG. 5) or writing a brand name on the article.

In another example, the method of manufacturing the 3D article includes molding, extruding, casting or a combination thereof a composition comprising at least 30% by weight of one or more active agents, optionally one or more auxiliary ingredients, for example one or more structurants, and optionally one or more additives.

Package

The 3D articles of the present invention may be enclosed in a package, individually wrapped and/or multi-article wrapped. In one example, the package exhibits a moisture barrier with a water vapor transmission rate of less than about 1.0 g H$_2$O/day/m$^2$ and/or less than about 0.5 g H$_2$O/day/m$^2$ and/or less than about 0.3 g H$_2$O/day/m$^2$ and/or about 0.1 g H$_2$O/day/m$^2$.

Method of Use

The present invention also provides for a method of using the 3D articles of the present invention to treat fabrics, for example to provide fabric conditioning benefits to fabrics during a drying process, for example an automatic clothes dryer drying process and/or in a washing machine operation and/or to treat hair, for example to provide hair conditioning benefits to hair during a treating process. In one example, a method of treating fabrics in an automatic clothes dryer drying process comprises the step of contacting a fabric with a 3D article according to the present invention within the dryer tub of an automatic clothes drying machine such that the fabric is treated. The step of contacting comprises the step of transferring (depositing) at least a portion of the 3D article's mass to the fabric, for example such that the mass of 3D article transferred to (deposited on) the fabric does not result in a stain on the fabric. It is believed that the fabric conditioning active agents are released from the 3D article of the present invention, due in part to the tumbling action and/or the heated air of the automatic clothes dryer.

In one example, the 3D article of the present invention is suitable for a single use, in other words, the 3D article is a consumable, single-use article, since it is designed to disappear in the automatic clothes dryer drying process. In other words, the 3D article, which is dry, for example dry-to-the-touch, is a dryer-added article that disappears and/or is entirely consumed and/or is entirely transferred to (deposited on) fabrics during use in the automatic clothes dryer drying process. "Dry-to-the-touch" as used herein means a 3D article is substantially free of liquids, for example water, such that it does not feel damp or wet prior to being subjected to water or other liquids. In other words, a dry-to-the-touch article of the present invention does not contain liquids, such as water. In one non-limiting example, a dry-to-the-touch article has a water content of less than about 20% and/or less than about 15% and/or less than about 10% and/or less than about 5% and/or less than about 3% and/or less than about 1% and/or about 0% as measured according to the Water Content Test Method described herein.

In one example, the 3D articles of the present invention may be used for imparting the fabric conditioning active agents to fabrics to provide fabric conditioning benefits such as softening, antistatic effects, and improved perfume deposition on the fabrics in an automatic clothes dryer. Generally, the method of using the 3D articles of the present invention comprises: commingling pieces of damp and/or dry fabric by tumbling the fabrics under heat in an automatic clothes dryer with one or more articles of the present invention. In one example, the 3D articles of the present invention exhibit a viscosity of less than about 2000 cps at 38° C. and a melting point greater than about 25° C. and/or from about 35° C. to about 100° C. such that the 3D article is flowable at automatic clothes dryer operating temperatures.

In one example, a method of treating fabrics in a washing machine process comprises the step of contacting a fabric with a 3D article according to the present invention within the washing machine tub such that the fabric is treated. The step of contacting comprises the step of transferring (depositing) at least a portion of the 3D article's mass to the fabric, for example such that the mass of 3D article transferred to (deposited on) the fabric does not result in a stain on the fabric. It is believed that the fabric conditioning active agents are released from the 3D article, due in part to the tumbling action and/or the water and/or heated air and/or water of the washing machine.

In one example, the 3D article of the present invention is suitable for a single use, in other words, the 3D article is a consumable, single-use article, since it is designed to disappear in the washing process, for example washing machine process. In other words, the 3D article, which is dry, for example dry-to-the-touch, is a dryer-added article that disappears and/or is entirely consumed and/or is entirely transferred to (deposited on) fabrics during use in the washing process, for example washing machine process. "Dry-to-the-touch" as used herein means a 3D article is substantially free of liquids, for example water, such that it does not feel damp or wet prior to being subjected to water or other liquids. In other words, a dry-to-the-touch article of the present invention does not contain liquids, such as water. In one non-limiting example, a dry-to-the-touch article has a water content of less than about 20% and/or less than about 15% and/or less than about 10% and/or less than about 5% and/or less than about 3% and/or less than about 1% and/or about 0% as measured according to the Water Content Test Method described herein.

In one example, the 3D articles of the present invention may be used for imparting the fabric conditioning active agents to fabrics to provide fabric conditioning benefits such as softening, antistatic effects, and improved perfume deposition on the fabrics in a washing machine. Generally, the method of using the 3D articles of the present invention comprises: commingling pieces of damp and/or wet fabrics by agitating and/or spinning and/or tumbling the fabrics in the presence of a wash liquor, for example water and optionally detergent, and optionally in the presence of heat in a washing machine with one or more articles of the present invention. In one example, the 3D articles of the present invention exhibit a viscosity of less than about 2000 cps at 38° C. and a melting point greater than about 25° C. and/or from about 35° C. to about 100° C. such that the 3D article is flowable under washing machine operating conditions and/or exhibits a lamellar structure as measured according to the Lamellar Structure Test Method.

In still another example, the 3D articles of the present invention may be massaged and/or kneaded into one's hair during a shampooing and/or conditioning operation for treating one's hair. In one example, the 3D articles of the present invention exhibit a viscosity of less than about 2000 cps at 38° C. and a melting point greater than about 25° C. and/or from about 35° C. to about 100° C. such that the 3D article is flowable under hair shampooing and/or hair conditioning operating conditions and/or exhibits a lamellar structure as measured according to the Lamellar Structure Test Method.

NON-LIMITING EXAMPLES

Non-limiting examples of 3D articles and 3D article-forming compositions according to the present invention as shown in Table 1 below can be made as follows:

a. adding one or more active agents to a metal beaker;
b. heating the metal beaker to 80° C. with stirring/agitation until a homogeneous fluid of active agents is formed;
c. maintaining the metal beaker at 80° C.; and
d. adding an auxiliary ingredient (3D article-forming material, such as a structurant) to the homogeneous fluid of active agents with stirring/agitation until the auxiliary ingredient is homogeneously dispersed and/or homogeneously dissolved within the homogeneous fluid of active agents resulting in a 3D article-forming composition that is ready for spinning into fibrous elements to form a fibrous structure and ultimately a 3D article; and
e. optionally adding optional ingredients, such as perfumes, for example perfume microcapsules, tackifiers, such as microcrystalline waxes to facilitate attaching the 3D article to the interior dryer drum, and other optional ingredients.

Example 1

Non-limiting examples of 3D Article-Forming Compositions and/or 3D Articles shown in Table 1 below are made as follows. Example of 3D Article-Forming Compositions are prepared gravimetrically at ambient temperature by combining all ingredients of a 3D Article-Forming Composition (active agents, auxiliary ingredients, if any, and optional ingredients, if any) in a glass jar. The jars are then placed in an oven at 80° C. until the ingredients have melted and then the 3D Article-Forming Compositions are stirred/mixed by hand to ensure that the ingredients are sufficiently blended together, for example homogeneously blended. The 3D Article-Forming Compositions are then ready for making into 3D Articles according to the present invention.

TABLE 1

| 3D Article-Forming Composition | Active Agents | Wt. % of Active Agents | Auxiliary Ingredients | Wt. % of Auxiliary Ingredients | Optional Ingredients | Wt. % of Optional Ingredients |
| --- | --- | --- | --- | --- | --- | --- |
| F1 | Quaternary Ammonium Compound | 58% | Clay | 8% | Perfume | 3% |
|  | Fatty Acid | 29% | — | — | Perfume Microcapsule | 2% |
| F2 | Quaternary Ammonium Compound | 47% | Clay | 6% | Perfume | 2% |
|  | Fatty Acid | 23% | Silica | 20% | Perfume Microcapsule | 2% |
| F3 | Quaternary Ammonium Compound | 52% | Clay | 7% | Perfume | 3% |
|  | Fatty Acid | 26% | Fumed Silica | 10% | Perfume Microcapsule | 2% |
| F4 | Quaternary Ammonium Compound | 47% | Clay | 28% | Perfume | 2% |
|  | Fatty Acid | 23% | — | — | Perfume Microcapsule | 2% |
| F5 | Quaternary Ammonium Compound | 57% | Clay | 8% | Perfume | 3% |
|  | Fatty Acid | 28% | PVP | 2% | Perfume Microcapsule | 2% |
| F6 | Quaternary Ammonium Compound | 41% | Clay | 6% | Perfume | 2% |
|  | Fatty Acid | 20% | Corn Starch | 30% | Perfume Microcapsule | 1% |
| F7 | Quaternary Ammonium Compound | 62% | — | — | Perfume | 3% |
|  | Fatty Acid | 33% | — | — | Perfume Microcapsule | 2% |

Example 2

Non-limiting examples of 3D Articles made from FDM 3D Printing are shown in Table 2 below. To make the FDM 3D printed 3D articles, CAD files are designed and converted to STL files. The 3D Article-Forming Compositions prepared as described above in Example 1 are added to a FDM 3D printer, commercially available, equipped with a heated syringe. The STL files are then sent to the FDM 3D printer to create 3D articles of the present invention of varying shape and properties, some of which are exemplified in Tables 2, 3, and 4 below. Table 2 below describes some grids (3D articles) that are printed.

TABLE 2

| Grid sample # | ND[1] [mm] | Width of square [mm] | Layers [#] | Space between lines [mm] | Angle of grid relative to previous layer [degrees] | Formula |
| --- | --- | --- | --- | --- | --- | --- |
| G1 | 0.5 | 89.4 | 2 | 2.5 | 90 | F1 |
| G2 | 0.5 | 63.8 | 4 | 2.5 | 90 | F1 |
| G3 | 0.5 | 44.7 | 8 | 2.5 | 90 | F1 |
| G4 | 0.5 | 114.0 | 2 | 4 | 90 | F1 |
| G5 | 0.5 | 80.4 | 4 | 4 | 90 | F1 |
| G6 | 0.5 | 57.4 | 8 | 4 | 90 | F1 |
| G7 | 0.5 | 89.4 | 2 | 2.5 | 45 | F1 |
| G8 | 0.5 | 63.8 | 4 | 2.5 | 45 | F1 |
| G9 | 0.5 | 44.7 | 8 | 2.5 | 45 | F1 |
| G10 | 0.5 | 114.0 | 2 | 4 | 45 | F1 |
| G11 | 0.5 | 80.4 | 4 | 4 | 45 | F1 |
| G12 | 0.5 | 57.4 | 8 | 4 | 45 | F1 |
| G13 | 0.5 | 54.8 | 4 | 2 | 90 | F2 |
| G14 | 0.5 | 63.7 | 4 | 2 | 90 | F3 |
| G15 | 0.5 | 63.7 | 4 | 2 | 90 | F4 |
| G16 | 0.5 | 48.8 | 4 | 2 | 90 | F5 |
| G17 | 0.7[2] | 55 | 1 | 0 | 90 | F1 |
| G18 | 0.7[2] | 55 | 2 | 3 | 90 | F1 |
| G19 | 0.7[3] | 55 | 2 | 3 | 90 | F1 |
| G20 | 0.7[2] | 55 | 2 | 5 | 90 | F1 |

[1]Nozzle Diameter;
[2]Measured flow rate of 10 g/min;
[3]Measured flow rate of 6 g/min

Example 3

Non-limiting examples of 3D Articles of the present invention are made from extruding the 3D Article-Forming Compositions described in Example 1 above. The 3D Article-Forming Compositions of Example 1 above are added to an extrusion system. The 3D Article-Forming Compositions are kept at a temperature of 55° C. and are pressurized to 200 PSI and extruded through a 0.7 mm diameter nozzle onto a build platform arranged at 40 inch distance away from the nozzle. Ambient temperature flow of cooling air is directed to the tip of the nozzle. The flow of cooling air is created by two opposite 9 inch×0.002 inch air knifes with an inlet air pressure 10 psi. The build platform is moved randomly during extrusion until about a 1 inch thick layer of randomly patterned 3D Article is built on the build platform. A semi-circular metal mold is then pressed onto the randomly patterned 3D Article while the 3D Article is still warm to form mini-dome 3D Articles ("D1"). The mini-dome 3D Articles (D1) are then removed from the build platform once fully cooled. Tables 3 and 4 below show properties of such a mini-dome 3D Article (D1).

Example 4

Non-limiting examples of dryer-added 3D Articles namely; G1, G2, G4, G5, G6, G7, G9, G10, G11, and G12, of Example 2 are made with fabric conditioning active agents of the present invention and are made according to Example 2 above. The 3D Articles are placed in an automatic clothes dryer with clothing wet from a washing operation. The automatic clothes dryer is run until clothing is dry, typically between 40 and 60 minutes. Afterwards the clothes (fabrics) are removed and visually assessed for stains from the clothes. Table 3 below shows the results of the assessment.

TABLE 3

| Sample | Visually observed staining |
|---|---|
| G1 | Some fabric stains |
| G2 | Little fabric stains |
| G4 | No fabric stains |
| G5 | Little fabric staining |
| G6 | Little fabric staining |
| G7 | Some fabric staining |
| G9 | Little fabric staining |
| G10 | No fabric staining |
| G11 | No fabric staining |
| G12 | No fabric staining |
| D1 | No fabric staining |

Example 5

Non-limiting examples of dryer-added 3D Articles namely; G17, G18, G19, G20, and D1 of Examples 2 and 3 above are made with fabric conditioning active agents of the present invention and are made according to Example 2 or 3 above. The 3D Articles are measured according to the corresponding Test Methods described herein. The results of the Test Methods are shown in Table 4 below.

the following test methods are conducted on samples that have been conditioned in a conditioned room at a temperature of 23° C.±1.0° C. and a relative humidity of 50%±2% for a minimum of 2 hours prior to the test. The samples tested are "usable units." "Usable units" as used herein means sheets, flats from roll stock, pre-converted flats, and/or single or multi-ply products. All tests are conducted under the same environmental conditions and in such conditioned room. Do not test samples that have defects such as wrinkles, tears, holes, and like. Samples conditioned as described herein are considered dry samples (such as "dry filaments") for testing purposes. All instruments are calibrated according to manufacturer's specifications.

Micro-CT 3D Article Measurement Method (μCT Test Method)

The micro-CT 3D article measurement method is utilized to measure the volume and surface area of a 3D article sample, from which a Surface Area to Volume ratio is calculated. Additionally, a minimum bounding box volume of a 3D article sample is measured along with its mass, from which a Bounding Box Density is calculated. These measurements are based on analysis of polygonal (triangulated point cloud) data generated on a microtomograph (micro-CT) instrument (a suitable instrument is the FlashCT available from Hytec, Los Alamos, N. Mex., or equivalent). To generate the data an x-ray beam is passed through an article sample mounted on a rotating stage, where some of the x-rays are attenuated by the sample. The extent of attenuation correlates to the mass of material the x-rays have to pass through. The transmitted x-rays continue on to the digital detector array and generate a 2D projection image of the sample. A 3D image of the article sample is generated by collecting several individual projection images of the sample as it is rotated, which are then reconstructed into a single 3D data set. The instrument is interfaced with a computer running software to control the image acquisition of the raw data (suitable software is ZxAcquire DDA v2.6.7.19698 available from Industrial Imaging Solutions, Santa Clara, Calif., or equivalent). The raw 2D projection data is reconstructed into a 3D image and converted to polygonal data using CT analysis software (a suitable software is efX-CT software v. 1.9.5.1 available from North Star Imaging, Rogers, Minn., or equivalent). The 3D polygonal data set is then analyzed using a 3D metrology software (a suitable software is Geomagic Studio 2014 available from 3D Systems, Rock Hill, S.C., or equivalent).

The FlashCT is a cone beam micro-CT with a shielded walk-in cabinet. A dismountable Viscom microfocus x-ray

TABLE 4

Figure 6:
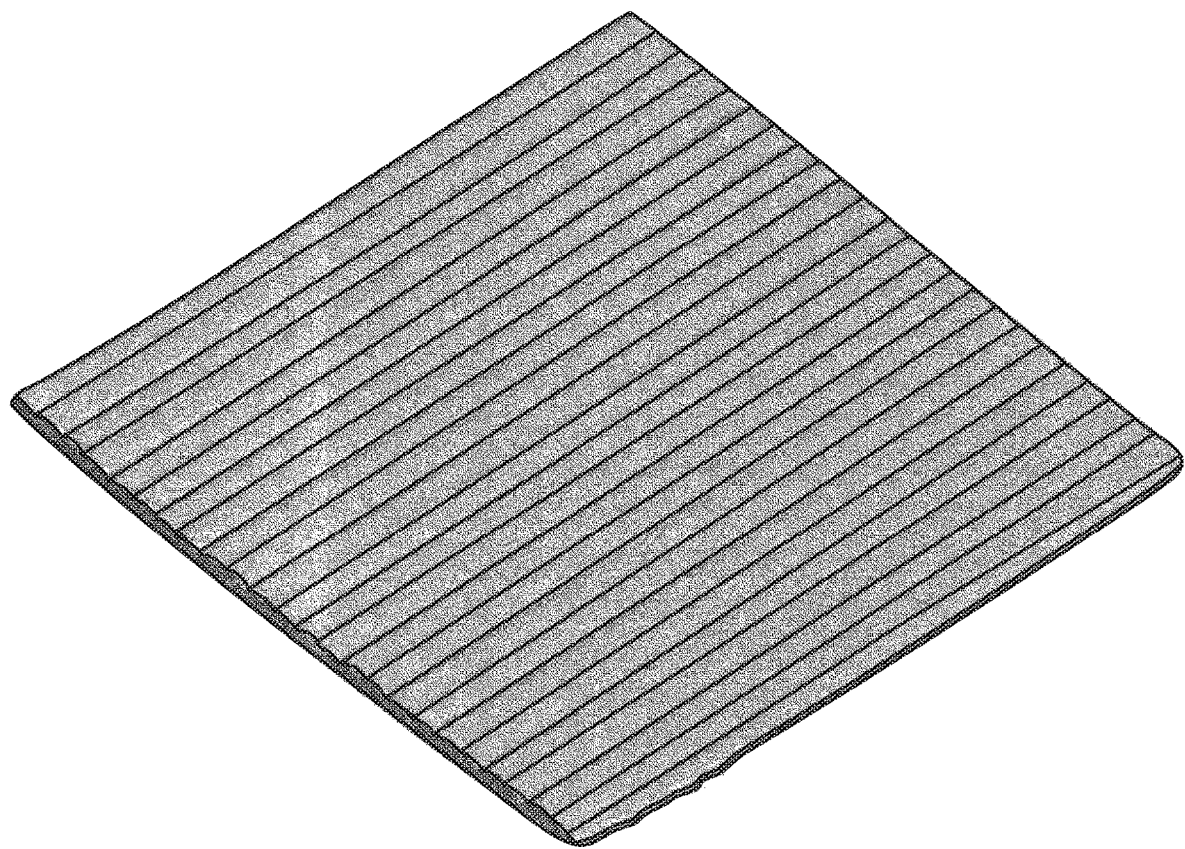
FIG. 6 is a μCT image of an example of a 3D article according to the present invention.
Figure 7:
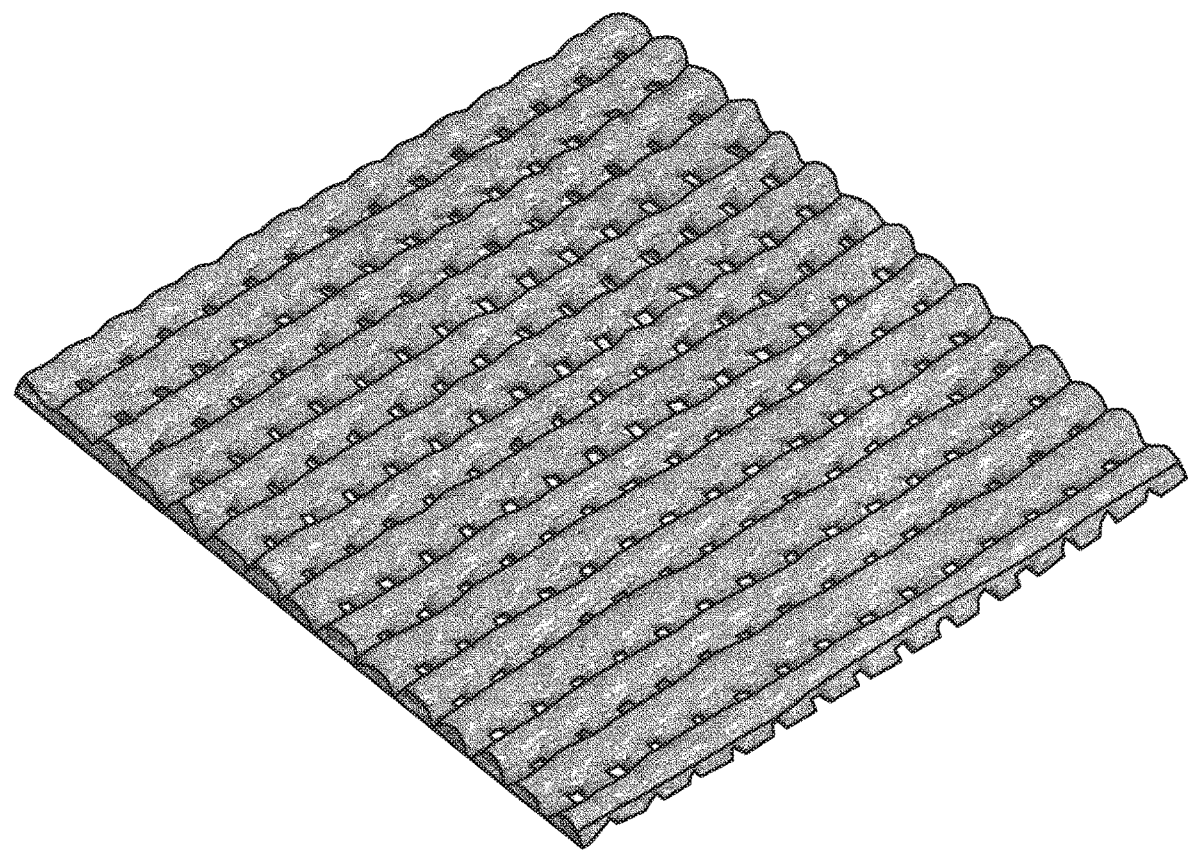
FIG. 7 is a μCT image of another example of a 3D article according to the present invention.
Figure 8:
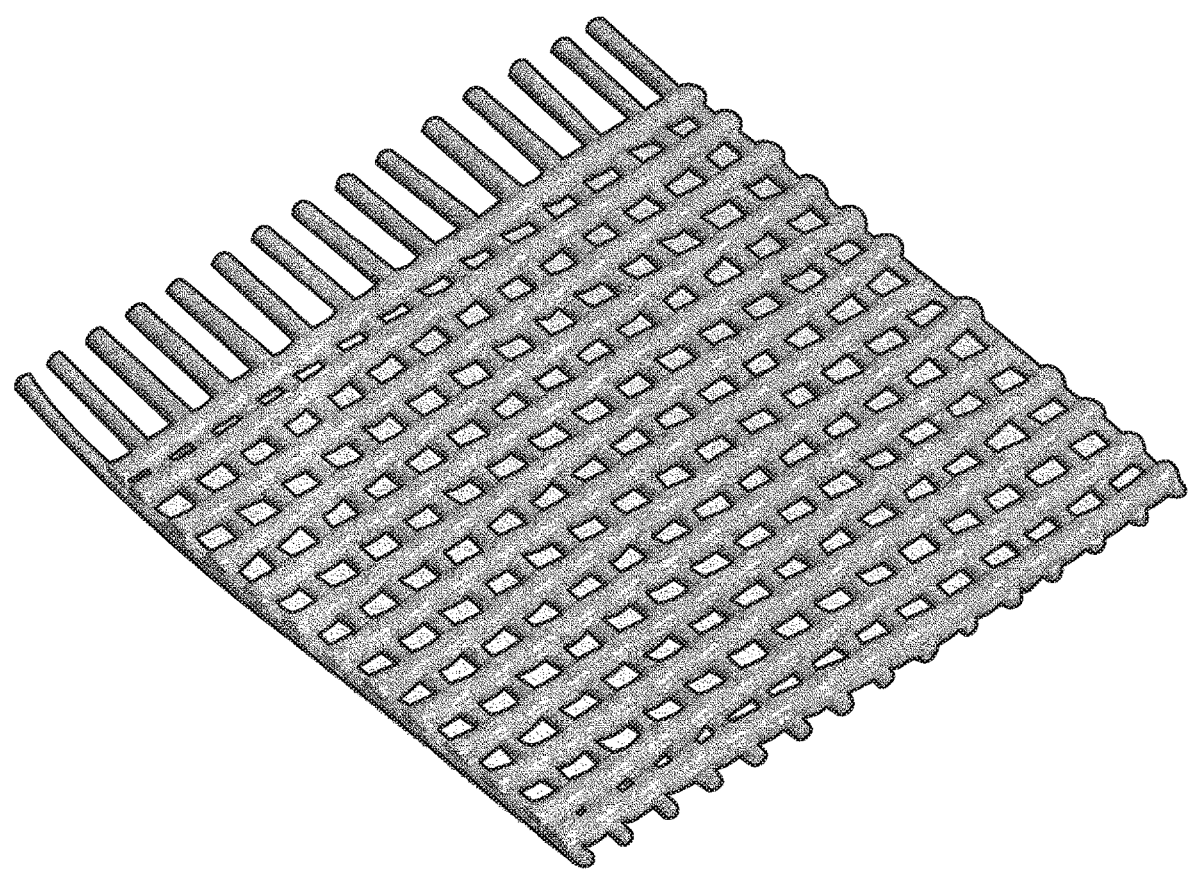
FIG. 8 is a μCT image of another example of a 3D article according to the present invention.
Figure 9:
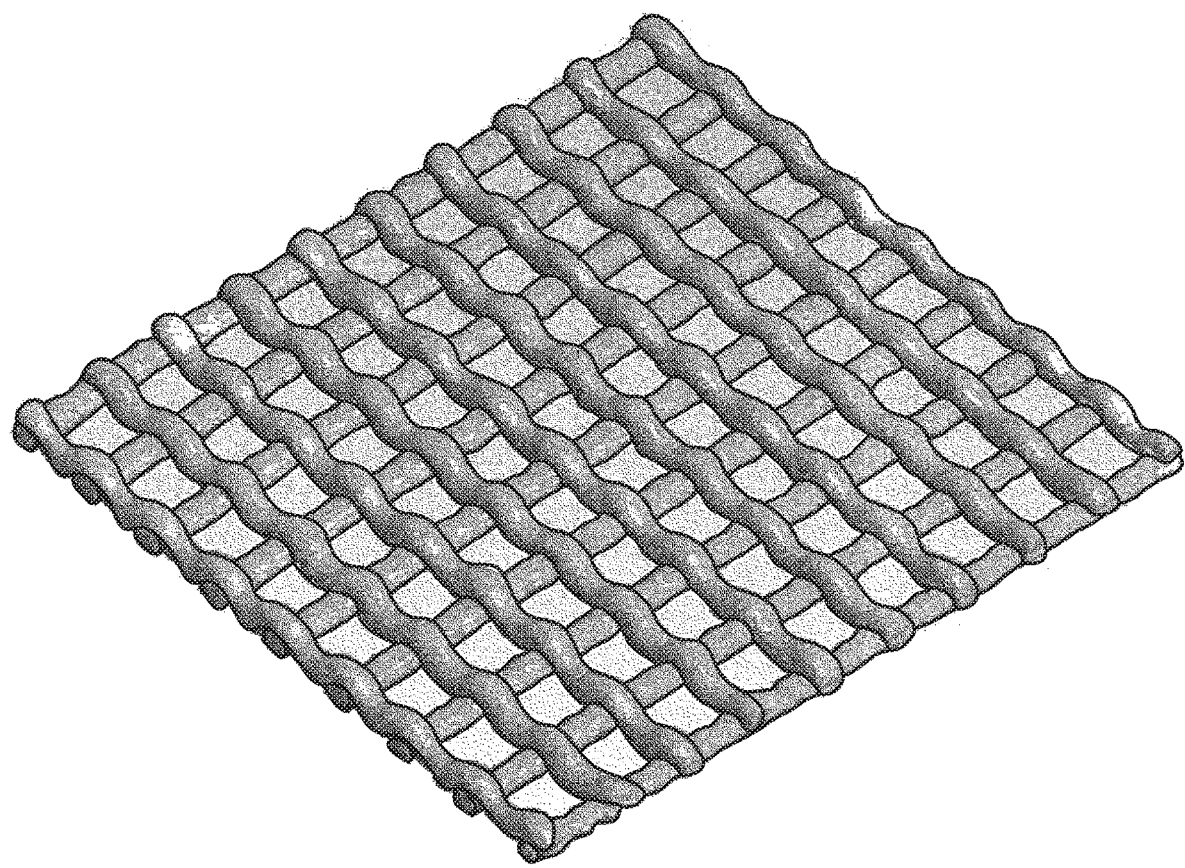
FIG. 9 is a μCT image of an example of a 3D article according to the present invention.
Figure 10:
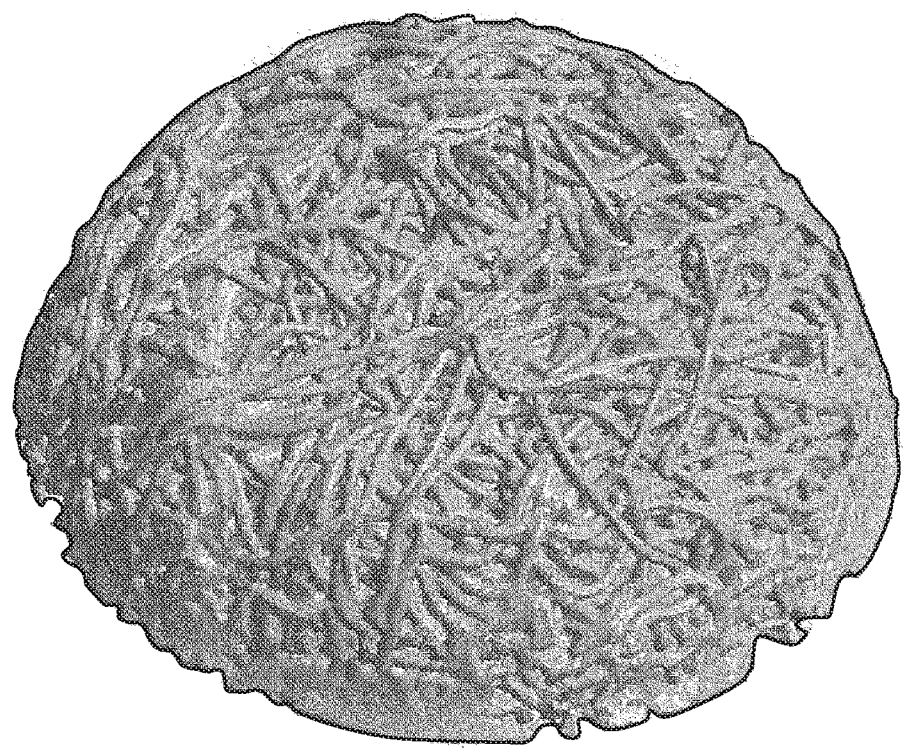
FIG. 10 is a μCT image of another example of a 3D article according to the present invention.

| Sample | 3D Article Free Melt Flow | Mass [g] | Visual Representation of microCT Data | Volume [mm³] | Surface Area [mm²] | Bounding Box Volume [mm³] | SA/Vol [1/mm] | Bounding Box Density [g/cm³] |
|---|---|---|---|---|---|---|---|---|
| Dryer Sheet | 0.6% | | | | | | | |
| G17 | — | 4.118 | FIG. 6 | 3989.8 | 6045.5 | 9279.3 | 1.52 | 0.44 |
| G18 | 77.4% | 5.182 | FIG. 7 | 5124.7 | 7804.6 | 10838.3 | 1.52 | 0.48 |
| G19 | — | 2.904 | FIG. 8 | 2995.8 | 6334.8 | 8770.9 | 2.11 | 0.33 |
| G20 | 74.7% | 2.724 | FIG. 9 | 2672.3 | 5189.0 | 8656.1 | 1.94 | 0.31 |
| D1 | 85.3% | 1.397 | FIG. 10 | 1352.1 | 10459.7 | 6841.6 | 7.74 | 0.21 |

Test Methods

Unless otherwise specified, all tests described herein including those described under the Definitions section and tube is used as the source with an adjustable diameter focal spot. The transmitted x-rays pass through a collimator, a scintillator (Lanex regular), and onto a 30×40 cm Varian (Paxscan) amorphous silicon digital detector. The x-ray tube is an XT9225-DED with a maximum energy of 225 keV and a current range of 10 µA to 3000 µA. The detector is located 880 mm from the source and runs at 5 frames per second.

The instrument is set up and calibrated according to the manufacturer's specifications. The article sample to be scanned is placed on top of a block of low density foam, such as Styrofoam or melamine foam, which will allow the signal from the article sample to be easily separated from its surroundings for analysis. The foam block and article sample are mounted onto the instrument's rotary table. Using the instrument control software, the scanning parameters are set to acquire a full 360 degree rotation of 2D projection images. The sample stage is located such that the size of the 3D image field of view contains the entire article sample, and the final resolution of the reconstructed 3D image has an isotropic voxel resolution of 30 µm (microns). Images are acquired with the x-ray source energy settings optimized to give the best contrast for the given sample material, but once optimized held constant for all substantially similar samples. For example, the appropriate energy settings for an article sample may be a voltage setting of 80 kVp and a current setting of 400 µA, with no additional low energy filter. At least 4 averages are collected to obtain a sufficient signal to noise for proper analysis. The raw data is saved in 32-bit floating point format to preserve the full detector output signal for analysis. Examples of µCT images are shown in FIGS. 6 to 10.

Using the CT analysis software, the raw 2D projection data is reconstructed into a 3D image. Once reconstructed, the 3D data set is threshold at a value which separates, and removes, the background signal due to air and foam, but maintains the signal from the article sample. The point cloud of the remaining signal from the article sample is converted into a polygonal mesh and saved in the appropriate 3D file format, such as STL.

The polygonal data of the article sample is opened in the 3D metrology software, and a closed volume created. Using the 3D metrology software the volume of the article sample is measured and recorded to the nearest 0.1 cubic mm ($mm^3$), the surface area of the article sample is measured and recorded to the nearest 0.1 square mm ($mm^2$), and the volume of a minimum bounding box of the article sample is measured and recorded to the nearest 0.1 cubic mm ($mm^3$). The minimum bounding box is the smallest rectangular box that can be drawn within which all of the points of the article sample lie.

After scanning in article sample in the micro-CT, the mass of the article sample is measured using a top loading analytical balance with a resolution of ±0.001 g, and is protected from air drafts and other disturbances using a draft shield. The mass of the article sample is measured and recorded to the nearest 0.001 g.

The Bounding Box Density is calculated by dividing the mass of the article sample by the volume of the article sample Bounding Box Volume in cubic centimeters (cc). The Bounding Box Density is calculated and reported to the nearest 0.01 g/cc.

The Surface Area to Volume Ratio is calculated by dividing the Surface Area of the article sample by the Volume of the article sample. The Surface Area to Volume Ratio is calculated and recorded to the nearest 0.01 1/mm ($mm^{-1}$).

Repeat this entire procedure on a total of five (5) substantially similar replicate 3D article samples, and report the Volume, Surface Area, Bounding Box Volume, Mass, Bounding Box Density, and Surface Area to Volume Ratio values as the average of the five individual measurements.

Mass Test Method

The mass of a 3D article is measured using a top loading analytical balance with a resolution of ±0.01 g, and is protected from air drafts and other disturbances using a draft shield. Prior to taking the mass measurement, properly condition the 3D article as previously described. After conditioning, measure the mass of the 3D article to the nearest 0.01 g. Measure and record the mass of ten (10) substantially similar replicate articles. Average together the 10 individual article mass measurements and report the value to the nearest 0.01 g.

Water Content Test Method

The water (moisture) content present in a 3D article is measured using the following Water Content Test Method. A 3D article sample, or portion thereof, is placed in a conditioned room at a temperature of 23° C.±1.0 C.° and a relative humidity of 50%±2% for at least 24 hours prior to testing. Under the temperature and humidity conditions mentioned above, using a balance with at least four decimal places, the weight of the sample is recorded every five minutes until a change of less than 0.5% of previous weight is detected during a 10 minute period. The final weight is recorded as the "equilibrium weight". Within 10 minutes, the samples are placed into a forced air oven on top of foil, or inside an aluminum tray for 24 hours at 70° C.±2 C.° at a relative humidity of 4%±2% for drying. After the 24 hours of drying, the sample is removed and weighed within 15 seconds. This weight is designated as the "dry weight" of the sample. The water (moisture) content of the sample is calculated according to the following equation:

$$\% \text{ Water Content} = \frac{\text{Equilibrium Weight} - \text{Dry Weight}}{\text{Dry Weight}} \times 100$$

The % Water Content is measured for 3 replicate samples, and averaged to give the reported to the nearest 0.1%.

Median Particle Size Test Method

This test method must be used to determine median particle size.

The median particle size test is conducted to determine the median particle size of the seed material using ASTM D 502-89, "Standard Test Method for Particle Size of Soaps and Other Detergents", approved May 26, 1989, with a further specification for sieve sizes used in the analysis. Following section 7, "Procedure using machine-sieving method," a nest of clean dry sieves containing U.S. Standard (ASTM E 11) sieves #8 (2360 um), #12 (1700 um), #16 (1180 um), #20 (850 um), #30 (600 um), #40 (425 um), #50 (300 um), #70 (212 um), #100 (150 um) is required. The prescribed Machine-Sieving Method is used with the above sieve nest. The seed material is used as the sample. A suitable sieve-shaking machine can be obtained from W.S. Tyler Company of Mentor, Ohio, U.S.A.

The data are plotted on a semi-log plot with the micron size opening of each sieve plotted against the logarithmic abscissa and the cumulative mass percent (Q3) plotted against the linear ordinate. An example of the above data representation is given in ISO 9276-1:1998, "Representation of results of particle size analysis—Part 1: Graphical Representation", Figure A.4. The seed material median particle size ($D_{50}$), for the purpose of the present disclosure, is defined as the abscissa value at the point where the cumulative mass percent is equal to 50 percent, and is calculated by a straight line interpolation between the data points directly above (a50) and below (b50) the 50% value using the following equation:

$$D_{50}=10^{\wedge}[\text{Log}(D_{a50})-(\text{Log}(D_{a50})-\text{Log}(D_{b50}))*(Q_{a50}-50\%)/(Q_{a50}-Q_{b50})]$$

where $Q_{a50}$ and $Q_{b50}$ are the cumulative mass percentile values of the data immediately above and below the 50$^{th}$ percentile, respectively; and $D_{a50}$ and $D_{b50}$ are the micron sieve size values corresponding to these data.

In the event that the 50$^{th}$ percentile value falls below the finest sieve size (150 um) or above the coarsest sieve size (2360 um), then additional sieves must be added to the nest following a geometric progression of not greater than 1.5, until the median falls between two measured sieve sizes.

The Distribution Span of the Seed Material is a measure of the breadth of the seed size distribution about the median. It is calculated according to the following:

$$\text{Span}=(D_{84}/D_{50}+D_{50}/D_{16})/2$$

Where $D_{50}$ is the median particle size and $D_{84}$ and $D_{16}$ are the particle sizes at the sixteenth and eighty-fourth percentiles on the cumulative mass percent retained plot, respectively.

In the event that the $D_{16}$ value falls below the finest sieve size (150 um), then the span is calculated according to the following:

$$\text{Span}=(D_{84}/D_{50}).$$

In the event that the $D_{84}$ value falls above the coarsest sieve size (2360 um), then the span is calculated according to the following:

$$\text{Span}=(D_{50}/D_{16}).$$

In the event that the $D_{16}$ value falls below the finest sieve size (150 um) and the $D_{84}$ value falls above the coarsest sieve size (2360 um), then the distribution span is taken to be a maximum value of 5.7.

3D Free Melt Flow Test Method

The 3D Free Melt Flow Parameter is determined using the 3D Free Melt Flow Test Method. In this method, an article is held at an elevated temperature for an extended period of time in close proximity to an absorbent medium, and the propensity of material from the article to melt, flow, and be absorbed by the absorbent medium is quantified.

Preparing the Absorbent Medium and Support Apparatus

The ambient conditions of the laboratory are 23±2° C. and 40±10% relative humidity. Sheets of Grade 4 filter paper having identical size and shape (such as Whatman 1004-150, GE Healthcare Bio-Sciences, or equivalent) are placed on top of one another to form a stack with uniform vertical edges. The size and shape of each piece of filter paper is selected so that the filter paper extends by at least 35 mm in all horizontal directions past the edges of the article when the article is placed on the central region of the uppermost piece of filter paper in the stack. The number of sheets of filter paper used in this stack is dependent on the mass of the article and its position as determined in the section "Determining the mass of the article and positioning article over the absorbent medium." Specifically, an effective basis weight is determined based on the article's mass and the article's approximate projected area onto the plane of the filter paper. For every 100 grams per square meter (gsm) of effective basis weight, one sheet of filter paper is used (rounding up to the next integral number of sheets for an effective basis weight falling between multiples of 100 gsm). The stack of filter paper is weighed and its mass is recorded to within ±0.01 g. This is the initial filter paper mass. The stack of filter paper is then placed onto a stainless steel grating (the lower grating) that extends beyond the edge of the filter paper. The grating is composed of solid parallel rods 3.4 mm in diameter and spaced 12.5 mm on center in a planar configuration. The grating comprises a frame or end rails to hold the rods in place, with the frame or rails beyond the outer edges of the filter paper. An identical grating (the upper grating) is then placed on top of the stack of filter paper such that the filter paper is captive between the two gratings (the grating assembly). The upper and lower gratings are oriented such that the constituent rods of the two gratings are parallel to each other and "registered" such that the rods of the two gratings are directly above one another in a vertical direction.

Determining the Mass of the Article and Positioning Article Over the Absorbent Medium The mass of the article to be analyzed is measured to within ±0.01 g. The article is placed on the top grating such that it is centered over the stack of filter paper with the filter paper extending at least 35 mm beyond the edges of the article in all horizontal directions. The article is placed in a stable orientation with its center of gravity as close as possible to the filter paper.

Exposure to Elevated Temperature and Gravimetric Analysis

This entire assembly is then placed (such that in an oven held at 80° C. for a duration of 24.0 hours. The racks are supported such that there is free space above the specimen and below the lower grating where the filter paper is positioned (that is, the lower grating does not rest on the oven floor).

At the end of the 24-hour period, the grating assembly is removed from the oven, and the filter paper is removed from the between the lower and upper gratings and allowed to re-equilibrate for 1 hour to ambient lab conditions. The mass of the filter paper along with any absorbed material from the article, defined as the final filter paper mass, is then determined to within ±0.01 g. The 3D Free Melt Flow Parameter is calculated according to the equation below:

$$\text{3D Free Melt Flow Parameter} = \frac{100\% \times (\text{Final Filter Paper Mass} - \text{Initial Filter Paper Mass})}{\text{Article Mass}}$$

The 3D Free Melt Flow Parameter is reported as a percent rounded to the nearest integer percent value.

3D Lamellar Structure Test Method

The Lamellar Structure Test Method makes use of small-angle x-ray scattering (SAXS) to determine if a lamellar structure is present in an article upon wetting after having been previously in a conditioned, dry state. Articles are conditioned at a temperature of 23° C.±2.0° C. and a relative humidity of 40%±10% for a minimum of 12 hours prior to the test. Articles conditioned as described herein are considered to be in a conditioned, dry state for the purposes of this invention. All instruments are calibrated according to manufacturer's specifications.

Sample Preparation

Three samples are analyzed upon wetting from the dry, conditioned state. Three separate representative articles are hydrated with water in order to achieve three separate preparations each possessing a different article-to-water mass ratio. The three different article-to-water mass ratios to be prepared are 1:5, 1:9, and 1:20. Each article is hydrated with a quantity of 23° C.±2.0° C. filtered deionized (DI) water sufficient to achieve the intended article-to-water mass ratio. Each of the three article/water mixtures (each corresponding to a different mass ratio) is stirred under low shear gently by hand at room temperature using a spatula until visibly homogenous. Each article/water mixture is then immediately loaded into a separate quartz capillary tube with outer diameter 2.0 mm in diameter and 0.01 mm wall thickness. The capillary tubes are immediately sealed with a sealant such as an epoxy resin to prevent the evaporation of water from the preparations. The sealant is permitted to dry for at least 2 hours and until dry at a temperature of 23° C.±2.0° C. prior to sample analysis. Each prepared wet sample is introduced into an appropriate SAXS instrument and data are collected.

Testing and Analysis

Samples are tested using SAXS in 2-dimension (2D) transmission mode over an angular range in of 0.3° to 3.0°2θ, to observe the presence and spacing of any intensity bands in the x-ray scattering pattern. The test is conducted using a SAXS instrument (such as the NanoSTAR, Bruker AXS Inc., Madison, Wis., U.S.A., or equivalent). Sealed liquid samples are analyzed in the instrument under vacuum. All samples are analyzed at a temperature of 23° C.±2.0° C. The x-ray tube of the instrument is operated at sufficient power to ensure that any scattering bands present are clearly detected. The beam diameter is 550±50 µm. One suitable set of operating conditions includes the following selections: NanoSTAR instrument; micro-focus Cu x-ray tube using the Kα line at 1.54 Å; 45 kV and 0.650 mA power; Vantec2K 2-Dimensional area detector; collection time of 1200 seconds; and distance between the sample and detector of 112.050 cm. The raw 2-D SAXS scattering pattern is integrated azimuthally to determine intensity (I) as a function of the scattering vector (q), which are expressed throughout this method units of reciprocal angstroms ($Å^{-1}$). The values for q are calculated by the SAXS instrument according to the following equation:

$$q = \frac{4\pi}{\lambda}\sin\theta$$

where:
2θ is the scattering angle; and
λ is the wavelength used.

For each integrated SAXS analyzed, the value of q in $Å^{-1}$ corresponding to each intensity peak on the plot of I vs q is identified and recorded from smallest to largest. (One of skill in the art knows that a sharp peak in q near the origin corresponds to scatter off of the beam stop and is disregarded in this method.) The value of q corresponding to the first intensity peak (the lowest value of q) is referred to as q*.

For each sample analyzed upon wetting from the dry, conditioned state, if an intensity peak is present at 2q*±0.002 $Å^{-1}$, the sample is determined to exhibit a lamellar structure, and the characteristic d-spacing parameter is defined as 2π/q*. If no intensity peak is present at 2q*±0.002 $Å^{-1}$, the sample is determined to not exhibit a lamellar structure. If a lamellar structure is determined to be present in at least any one of the three article/water ratios prepared, then the material of which the articles are composed is determined to exhibit a lamellar structure upon wetting. If no intensity peak is present at 2q*±0.002 $Å^{-1}$, in any of the three article/water ratios prepared, then the material of which the articles is composed is determined to not exhibit a lamellar structure upon wetting.

3D Article Composition Test Method

In order to prepare 3D articles for 3D article composition measurement, the 3D articles must be conditioned by removing any coating compositions and/or materials present on the external surfaces of the 3D articles that are removable. An example of a method for doing so is washing the 3D articles 3 times with a suitable solvent that will remove the external coating while leaving the 3D articles unaltered. The 3D articles are then air dried at 23° C.±1.0° C. until the 3D articles comprise less than 10% moisture. A chemical analysis of the conditioned 3D articles is then completed to determine the compositional make-up of the 3D articles with respect to the 3D article-forming materials and the active agents and the level of the 3D article-forming materials and active agents present in the fibrous elements.

The compositional make-up of the 3D articles with respect to the 3D article-forming material and the active agents can also be determined by completing a cross-section analysis using TOF-SIMs or SEM. Still another method for determining compositional make-up of the 3D articles uses a fluorescent dye as a marker. In addition, as always, a manufacturer of 3D articles should know the compositions of their 3D articles.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumable, single use, three-dimensional (3D) article comprising a solid 3D article, wherein the solid 3D article comprises:

a. one or more active agents present in the solid 3D article; and b. optionally, one or more auxiliary ingredients;

wherein the solid 3D article disappears during automatic clothes dryer use;

wherein the consumable, single use, 3D article exhibits a Bounding Box Density of less than about 0.98 g/cm³ as measured according to the µCT Test Method; and wherein the consumable, single use, 3D article exhibits a Free Melt Flow of more than about 20% as measured according to the Free Melt Flow Test Method.

2. The consumable, single use, 3D article according to claim 1 wherein at least one of the one or more active agents comprises an active agent selected from the group consisting of: fabric conditioning active agents, hair conditioning active agents, and mixtures thereof.

3. The consumable, single use, 3D article according to claim 2 wherein the fabric conditioning active agent is selected from the group consisting of: fatty acids, fatty acid derivatives, sulfonic acid derivatives, quaternary ammonium compounds, tertiary amines and salts thereof, nonionic surfactants, fatty alcohols, cationic surfactants, nonionic surfactants, zwitterionic surfactants, and mixtures thereof.

4. The consumable, single use, 3D article according to claim 3 wherein the fabric conditioning active agent comprises a fatty acid selected from the group consisting of: myristic acid, stearic acid, isostearic acid, cetearic acid, dodecanoic acid, linoleic acid, oleic acid, palmitic acid, lauric acid, and mixtures thereof.

5. The consumable, single use, 3D article according to claim 3 wherein the fabric conditioning active agent comprises a quaternary ammonium compound selected from the group consisting of: di(tallowyloxyethyl)hydroxyethylmethylammoniummethylsulfate, dimethyl bis(stearoyl oxyethyl) ammonium chloride, dimethyl bis(tallowyloxyethyl)ammonium chloride, dimethyl bis(tallowyloxyisopropyl) ammonium methylsulfate, and mixtures thereof.

6. The consumable, single use, 3D article according to claim 3 wherein the fabric conditioning active agent comprises a fatty alcohol selected from the group consisting of: cetyl alcohol, stearyl alcohol, behenyl alcohol, lauryl alcohol, myristic alcohol, isostearyl alcohol, arachidyl alcohol, and mixtures thereof.

7. The consumable, single use, 3D article according to claim 3 wherein the fabric conditioning active agent comprises an active agent selected from the group consisting of: $C_{15}$ or higher quaternary ammonium compound or salt thereof, tertiary amine or salt thereof, and mixtures thereof.

8. The consumable, single use, 3D article according to claim 3 wherein the fabric conditioning agent comprises a fatty alcohol and a quaternary ammonium compound.

9. The consumable, single use, water-insoluble 3D article according to claim 8 wherein the fatty alcohol and quaternary ammonium compound are present in the consumable, single use, water-insoluble 3D article at a weight ratio of greater than 1:1.

10. The consumable, single use, 3D article according to claim 3 wherein the fabric conditioning active agent comprises a fatty acid and a quaternary ammonium compound.

11. The consumable, single use, water-insoluble 3D article according to claim 10 wherein the fatty acid and quaternary ammonium compound are present in the consumable, single use, water-insoluble 3D article at a weight ratio of greater than 1:1.

12. The consumable, single use, 3D article according to claim 1 wherein at least one of the one or more active agents is selected from the group consisting of: perfumes, builders, chelants, antioxidants, brighteners, sun fade inhibiting agents, UV absorbing agents, insect repellants, scents, bleaching agents, enzymes, antimicrobials, antibacterials, antifungals, perfume delivery systems, perfume microcapsules, dye transfer inhibiting agents, hueing dyes, soil release agents, colorants, preservatives, opacifiers, stabilizers, anti-shrinkage agents, anti-wrinkle agents, soil release agents, fabric crisping agents, reductive agents, spotting agents, germicides, fungicides, anti-corrosion agents, and mixtures thereof.

13. The consumable, single use, water-insoluble 3D article according to claim 1 wherein the consumable, single use, water-insoluble 3D article further comprises one or more optional ingredients selected from the group consisting of: polymers, perfumes, pro-perfumes, finishing aids, malodor control and removal agents, odor neutralizers, polymeric dye transfer inhibiting agents, cationic deposition enhancing polymers, builders, heavy metal ion sequestrants, surfactants, suds stabilizing polymers, pH modifiers, buffering agents, alkalinity sources, fabric softeners, antistatic agents, dye fixatives, dye abrasion inhibitors, wrinkle reduction agents, wrinkle resistance agents, wrinkle release agents, silicones, soil release polymers, soil repellency agents, colorants, pigments, bittering agents, anti-redeposition agents, bleach activators, bleach catalysts, bleach boosters, bleaches, photobleaches, enzymes, coenzymes, enzyme stabilizers, crystal growth inhibitors, anti-tarnishing agents, anti-oxidants, metal ion salts, corrosion inhibitors, antiperspirant, zinc pyrithione, plant derivatives, plant extracts, plant tissue extracts, plant seed extracts, plant oils, botanicals, botanical extracts, essential oils, skin sensates, astringents, anti-acne agents, anti-dandruff agents, antifoaming agents, cosmetic astringents, cosmetic biocides, denaturants, drug astringents, external analgesics, film formers or materials, skin bleaching and lightening agents, skin-conditioning agents, skin soothing and/or healing agents and derivatives, skin treating agents, sunscreen agents, insect repellants, vitamins, anti-bacterial agents, anti-microbial agents, antifungal agents, sun fade inhibiting agents, UV absorbing agents, antioxidants, scents, perfume delivery systems, hueing dyes, chelants, brighteners, antimicrobials, antibacterials, and mixtures thereof.

14. The consumable, single use, 3D article according to claim 1 wherein the solid 3D article further comprises one or more auxiliary ingredients.

15. The consumable, single use, 3D article according to claim 14 wherein the auxiliary ingredient comprises a structurant.

16. The consumable, single use, 3D article according to claim 15 wherein the structurant is present in the solid 3D article at a level of from about 1% to about 50% by weight on a dry solid 3D article basis.

17. The consumable, single use, water-insoluble 3D article according to claim 1 wherein the consumable, single use, water-insoluble 3D article exhibits a lamellar structure response as measured according to the Lamellar Structure Test Method.

18. The consumable, single use, water-insoluble 3D article according to claim 1 wherein the consumable, single use, water-insoluble 3D article exhibits a lamellar structure response in a wet state but does not exhibit a lamellar structure response in a dry state as measured according to the Lamellar Structure Test Method.

19. The consumable, single use, water-insoluble 3D article according to claim 1 wherein the consumable, single use, water-insoluble 3D article exhibits a water content of from about 0% to about 20% as measured according to the Water Content Test Method.

* * * * *